US012729298B2

(12) United States Patent
Klun et al.

(10) Patent No.: US 12,729,298 B2
(45) Date of Patent: Sep. 8, 2026

(54) ORTHODONTIC ARTICLES COMPRISING POLYESTER URETHANE (METH)ACRYLATE POLYMER AND MONOFUNCTIONAL (METH)ACRYLATE MONOMER, METHODS, AND POLYMERIZABLE COMPOSITIONS

(71) Applicant: Solventum Intellectual Properties Company, Maplewood, MN (US)

(72) Inventors: Thomas P. Klun, Lakeland, MN (US); Richard J. Pokorny, Maplewood, MN (US); Chad M. Amb, Roberts, WI (US); Benjamin R. Coonce, South St. Paul, MN (US); Tianyu Wu, St. Paul, MN (US); Saswata Chakraborty, Cottage Grove, MN (US); Yongshang Lu, Woodbury, MN (US); Benjamin C. Mac Murray, Minneapolis, MN (US); Robert S. Clough, St. Paul, MN (US); Ahmed S. Abuelyaman, Woodbury, MN (US); John M. Riedesel, San Jose, CA (US)

(73) Assignee: Solventum Intellectual Properties Company, Eagan, MN (US)

(*) Notice: Subject to any disclaimer, the term of this patent is extended or adjusted under 35 U.S.C. 154(b) by 644 days.

(21) Appl. No.: 17/287,603

(22) PCT Filed: Oct. 31, 2019

(86) PCT No.: PCT/IB2019/059351

§ 371 (c)(1),
(2) Date: Apr. 22, 2021

(87) PCT Pub. No.: WO2020/104873

PCT Pub. Date: May 28, 2020

(65) Prior Publication Data

US 2022/0056258 A1 Feb. 24, 2022

Related U.S. Application Data

(60) Provisional application No. 62/769,081, filed on Nov. 19, 2018, provisional application No. 62/850,747, filed on May 21, 2019.

(51) Int. Cl.
*A61K 6/90* (2020.01)
*A61C 7/08* (2006.01)
(Continued)

(52) U.S. Cl.
CPC ................ *C08L 51/08* (2013.01); *A61C 7/08* (2013.01); *A61K 6/893* (2020.01); *A61K 6/90* (2020.01);
(Continued)

(58) Field of Classification Search
CPC . C08L 51/08; C08L 75/16; A61C 7/08; A61K 6/90; A61K 6/893; B33Y 70/00; B33Y 80/00
(Continued)

(56) References Cited

U.S. PATENT DOCUMENTS

| | | | |
|---|---|---|---|
| 3,429,722 | A | 2/1969 | Economy |
| 3,795,524 | A | 3/1974 | Sowman |

(Continued)

FOREIGN PATENT DOCUMENTS

| | | |
|---|---|---|
| CA | 1012275 | 6/1977 |
| CA | 1139486 | 1/1983 |

(Continued)

OTHER PUBLICATIONS

Figueroa et al, Thermal behavior of poly(2-hydroxyethyl methacrylate . . . ) network, 2013, Materials Science and Engineering, 45, 012005. (Year: 2013).*

(Continued)

*Primary Examiner* — Ruiyun Zhang

(57) ABSTRACT

In one embodiment, an orthodontic article is described comprising the reaction product of a polymerizable composition comprising: a) 30-70 parts by weight of monofunctional (meth)acrylate monomer, wherein a cured homopolymer of at least one monofunctional (meth)acrylate monomer has a Tg of at least 30, 35, 40, 45, 50, 55, or 60° C.; and b) urethane (meth)acrylate polymer comprising polymerized units of an aliphatic polyester diol. Also described are polymerizable compositions, as well as methods and systems for making an article utilizing 3D printing.

20 Claims, 7 Drawing Sheets

(51) Int. Cl.

| | |
|---|---|
| ***A61K 6/893*** | (2020.01) |
| ***B29C 64/135*** | (2017.01) |
| ***B33Y 10/00*** | (2015.01) |
| ***B33Y 30/00*** | (2015.01) |
| ***B33Y 70/00*** | (2020.01) |
| ***B33Y 80/00*** | (2015.01) |
| ***C08L 51/08*** | (2006.01) |
| ***C08L 75/16*** | (2006.01) |
| *B29K 33/00* | (2006.01) |
| *B29L 31/00* | (2006.01) |

(52) U.S. Cl.
CPC ............ *B29C 64/135* (2017.08); *B33Y 10/00* (2014.12); *B33Y 30/00* (2014.12); *B33Y 70/00* (2014.12); *B33Y 80/00* (2014.12); *C08L 75/16* (2013.01); *A61C 2201/00* (2013.01); *B29K 2033/08* (2013.01); *B29L 2031/753* (2013.01)

(58) Field of Classification Search
USPC .......................................................... 523/109
See application file for complete search history.

(56) References Cited

U.S. PATENT DOCUMENTS

| | | | | |
|---|---|---|---|---|
| 4,047,965 | A | 9/1977 | Karst | |
| 4,182,829 | A | 1/1980 | Walkowiak | |
| 4,264,752 | A | 4/1981 | Watson, Jr. | |
| 4,591,626 | A | 5/1986 | Kawai | |
| 4,761,136 | A | 8/1988 | Madhavan | |
| 4,787,850 | A | 11/1988 | Michl | |
| 4,942,001 | A | 7/1990 | Murphy | |
| 4,952,241 | A | 8/1990 | Reiners | |
| 4,954,462 | A | 9/1990 | Wood | |
| 4,968,725 | A | 11/1990 | Mukai | |
| 5,185,299 | A | 2/1993 | Wood | |
| 5,780,154 | A | 7/1998 | Okano | |
| 5,849,270 | A | 12/1998 | Podszun | |
| 5,863,486 | A | 1/1999 | Ozaki et al. | |
| 5,981,621 | A | 11/1999 | Clark | |
| 6,017,973 | A | 1/2000 | Tamura | |
| 6,183,593 | B1 | 2/2001 | Narang | |
| 6,200,732 | B1 | 3/2001 | Tamura | |
| 6,426,373 | B1 | 7/2002 | Stange | |
| 6,432,426 | B2 | 8/2002 | Kessler | |
| 6,579,517 | B1 | 6/2003 | Kim | |
| 6,617,413 | B1 | 9/2003 | Bruchmann | |
| 6,833,425 | B1 | 12/2004 | Hecht | |
| 7,001,953 | B2 | 2/2006 | Chen | |
| 7,666,970 | B2 | 2/2010 | Weikard | |
| 7,977,406 | B2 | 7/2011 | Hsieh | |
| 8,044,235 | B2 | 10/2011 | Nozawa | |
| 8,703,897 | B2 | 4/2014 | Gan | |
| 8,729,202 | B2 | 5/2014 | Mayadunne | |
| 8,735,464 | B2 | 5/2014 | Skaria | |
| 8,853,294 | B2 | 10/2014 | Myung | |
| 8,865,790 | B2 | 10/2014 | Koltisko | |
| 9,066,992 | B2 | 6/2015 | Stankus | |
| 9,115,245 | B2 | 8/2015 | Sahatjian | |
| 9,205,601 | B2 | 12/2015 | Desimone | |
| 9,360,757 | B2 | 6/2016 | Desimone | |
| 9,610,377 | B2 | 4/2017 | Hissink | |
| 9,738,748 | B2 | 8/2017 | Takenouchi | |
| 9,757,493 | B2 | 9/2017 | Lin | |
| 10,703,929 | B2 | 7/2020 | Berger et al. | |
| 2005/0089630 | A1 | 4/2005 | Schlunt | |
| 2006/0258578 | A1 | 11/2006 | Weber | |
| 2007/0031791 | A1 | 2/2007 | Cinader, Jr. | |
| 2008/0031918 | A1 | 2/2008 | Lawin | |
| 2008/0248442 | A1 | 10/2008 | Raby | |
| 2010/0273901 | A1 | 10/2010 | Ehrenberg | |
| 2011/0091832 | A1 | 4/2011 | Kim | |
| 2012/0021383 | A1 | 1/2012 | Skaria | |
| 2012/0088090 | A1 | 4/2012 | Miyazaki et al. | |
| 2012/0270038 | A1* | 10/2012 | Kim | C08F 290/067 525/454 |
| 2013/0095446 | A1 | 4/2013 | Andreiko | |
| 2014/0239527 | A1 | 8/2014 | Lee | |
| 2014/0356799 | A1 | 12/2014 | Cinader, Jr. | |
| 2015/0072083 | A1 | 3/2015 | Nebioglu et al. | |
| 2015/0209477 | A1 | 7/2015 | Lian | |
| 2016/0311163 | A1 | 10/2016 | Yasukochi | |
| 2016/0326383 | A1 | 11/2016 | Pokorny et al. | |
| 2017/0007362 | A1 | 1/2017 | Chen | |
| 2017/0158803 | A1 | 6/2017 | Amin | |
| 2019/0374309 | A1 | 12/2019 | Parkar | |
| 2020/0362157 | A1* | 11/2020 | Parkar | C08F 220/1808 |
| 2021/0176820 | A1 | 6/2021 | Zhang | |
| 2021/0186820 | A1 | 6/2021 | Chakraborty | |
| 2021/0315668 | A1* | 10/2021 | Achten | A61C 7/08 |

FOREIGN PATENT DOCUMENTS

| | | | |
|---|---|---|---|
| CN | 105899623 | A | 8/2016 |
| CN | 107922573 | A | 4/2018 |
| CN | 109016496 | A | 12/2018 |
| JP | H06-017378 | | 1/1994 |
| JP | H08-188630 | | 7/1996 |
| JP | 2000085018 | A | 3/2000 |
| JP | 3055166 | | 6/2000 |
| JP | 3115792 | | 12/2000 |
| JP | 3301447 | | 7/2002 |
| JP | 2004-217809 | | 8/2004 |
| JP | 2005068331 | A | 3/2005 |
| JP | 4403312 | | 1/2010 |
| JP | 2010-043194 | | 2/2010 |
| JP | 4488123 | | 4/2010 |
| JP | 4526056 | | 8/2010 |
| JP | 4682544 | | 5/2011 |
| JP | 4880248 | | 2/2012 |
| JP | 4941794 | | 5/2012 |
| JP | 2012-184385 | | 9/2012 |
| JP | 5055764 | | 10/2012 |
| JP | 5068513 | | 11/2012 |
| JP | 5224965 | | 7/2013 |
| JP | 2013170215 | A | 9/2013 |
| JP | 5377201 | | 12/2013 |
| JP | 5445215 | | 3/2014 |
| JP | 2014-114444 | | 6/2014 |
| JP | 2014-116295 | | 6/2014 |
| JP | 5586965 | | 9/2014 |
| JP | 2016-112824 | | 6/2016 |
| JP | 2017-048288 | | 3/2017 |
| JP | 2017-210539 | | 11/2017 |
| JP | 2017-210579 | | 11/2017 |
| WO | WO 1991-003503 | | 3/1991 |
| WO | WO 1996-004648 | | 2/1996 |
| WO | WO 1996-015179 | | 5/1996 |
| WO | WO 1998-021157 | | 5/1998 |
| WO | WO 2006-005772 | | 1/2006 |
| WO | WO 2007-022503 | | 2/2007 |
| WO | WO 2007-129704 | | 11/2007 |
| WO | WO 2009-045752 | | 4/2009 |
| WO | WO 2009-142074 | | 11/2009 |
| WO | WO 2010-125373 | | 11/2010 |
| WO | WO 2012-045660 | | 4/2012 |
| WO | WO 2014-077688 | | 5/2014 |
| WO | WO 2015-094842 | | 6/2015 |
| WO | WO 2016-109660 | | 7/2016 |
| WO | WO 2016-148960 | | 9/2016 |
| WO | WO 2016-149007 | | 9/2016 |
| WO | WO 2017-009184 | | 1/2017 |
| WO | WO 2017-020859 | | 2/2017 |
| WO | WO 2017-047615 | | 3/2017 |
| WO | WO 2017-208959 | | 12/2017 |
| WO | WO 2018-005501 | | 1/2018 |
| WO | WO 2018-033296 | | 2/2018 |
| WO | WO 2018-119026 | | 6/2018 |
| WO | WO 2019-023009 | | 1/2019 |
| WO | WO 2019-023120 | | 1/2019 |
| WO | WO 2019-023166 | | 1/2019 |
| WO | WO 2019-048963 | | 3/2019 |
| WO | WO 2019-103855 | | 5/2019 |

(56) References Cited

FOREIGN PATENT DOCUMENTS

| | | |
|---|---|---|
| WO | WO 2019-104072 | 5/2019 |
| WO | WO 2019-104079 | 5/2019 |
| WO | WO 2019-119026 | 6/2019 |
| WO | WO 2019-175716 | 9/2019 |
| WO | WO 2019-224699 | 11/2019 |
| WO | WO 2019-244007 | 12/2019 |
| WO | WO 2020-003169 | 1/2020 |
| WO | WO 2020-003197 | 1/2020 |
| WO | WO 2020-005411 | 1/2020 |
| WO | WO 2020-005413 | 1/2020 |

OTHER PUBLICATIONS

Parrod, et al. "Polyacrylamides dérivés d'amides cycliques," Journal of Polymer Science, vol. XXIX, pp. 411-416, (1958), Prague Symposium.

Fang, "The influence of monobutyl itaconate and β-carboxyethyl acrylate on acrylic latex pressure sensitive adhesives", International Journal of Adhesion and Adhesives, Aug. 2018, vol. 84, pp. 387-393.

Fleischhaker, "Glass-Transition-, Melting-, and Decomposition Temperatures of Tailored Polyacrylates and Polymethacrylates: General Trends and Structure-Property Relationships", Macromolecular Chemistry and Physics, Jun. 2014, vol. 215, No. 12, pp. 1192-1200.

Hopfinger, "Molecular Modeling of Polymers. IV. Estimation of Glass Transition Temperatures", Journal of Polymer Science: Part B: Polymer Physics, Sep. 1988, vol. 26, No. 10, pp. 2007-2028.

Jakubowski, "Comparison of thermomechanical properties of statistical, gradient and block copolymers of isobornyl acrylate and n-butyl acrylate with various acrylate homopolymers", Polymer, Mar. 2008, vol. 49, No. 06, pp. 1567-1578.

Matsumoto, "Synthesis and Thermal Properties of Poly (cycloalkyl methacrylate) s Bearing Bridged- and Fused-Ring Structures", Journal of Polymer Science: Part A Polymer Chemistry, Sep. 1993, vol. 31, No. 10, pp. 2531-2539.

Matsumoto, "Synthesis and Characterization of Poly(1-adamantyl methacrylate): Effects of the Adamantyl Group on Radical Polymerization Kinetics and Thermal Properties of the Polymer", Macromolecules, Jul. 1991, vol. 24, No. 14, pp. 4017-4024.

Matsumoto, "Radical Polymerization of 4-tert-Butylcyclohexyl Methacrylate: Polymerization Kinetics and Polymer Properties", Macromolecules, Mar. 1993, vol. 26 No. 7, pp. 1659-1665.

"Methacrylate Resins", By E. I. du Pont de Nemours & Company, Inc., at the Ninety-second Meeting of the American Chemical Society at Pittsburgh, Pa., Industrial and Engineering Chemistry, Sep. 1936, vol. 28, No. 10, pp. 1160-1163.

"Methyl Methacrylate MMA", Product of Mitsubishi Chemical Corporation, XP055659748, <Retrieved from the Internet on Jan. 2020>, URL <https//www m-chemical co jp/en/products/departments/mcc/chemicals-dept/product/ 1201253 7952 html>, 3 pages.

Russell, "Thermal and Dynamic Mechanical Relaxation Behavior of Stereoregular Poly(2-Hydroxyethyl Methacrylate)", Journal of Polymer Science: Polymer Physics Edition, Jun. 1980, vol. 18, No. 06, pp. 1271-1283.

Song, "In Vitro Evaluation of Chemically Cross-Linked Shape-Memory Acrylate-Methacrylate Copolymer Networks as Ocular Implants", The Journal of Physical Chemistry B, Jun. 2010, vol. 114, No. 21, pp. 7172-7178.

Turner, "The glass transition temperature of poly(N-vinyl pyrrolidone) by differential scanning calorimetry", Polymer, May 1985, vol. 26, No. 5, pp. 757-762.

Wilson, "Thermal Expansion of Amorphous Polymers at Atmospheric Pressure. I. Experimental", Macromolecules, Nov. 1973, vol. 6, No. 6, pp. 902-908.

International Search Report for PCT International Application No. PCT/IB2019/059351, mailed on Feb. 6, 2020, 5 pages.

* cited by examiner

ORTHODONTIC ARTICLES COMPRISING POLYESTER URETHANE (METH)ACRYLATE POLYMER AND MONOFUNCTIONAL (METH)ACRYLATE MONOMER, METHODS, AND POLYMERIZABLE COMPOSITIONS

BACKGROUND 3D printing can be used to fabricate orthodontic clear tray aligners. Orthodontic clear tray aligners are provided in a series and are intended to be worn in succession, over a period of months, to gradually move teeth in incremental steps towards a desired target arrangement. Some types of clear tray aligners have a row of tooth-shaped receptacles for receiving each tooth of the patient's dental arch, and the receptacles are oriented in slightly different positions from one appliance to the next to incrementally urge each tooth toward its desired target position by virtue of the resilient properties of the polymeric material.

SUMMARY

Existing 3D printable/polymerizable resins tend to be too brittle (e.g., fail to yield and exhibit low elongation) for a resilient oral appliance such as an aligner. Even cured compositions that are not brittle when dry may lose their strength after being exposed to an (e.g. aqueous) oral environment. On the other hand, an aligner or other appliance prepared from such resins could be too soft and flexible, and not exert the force needed to move teeth. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in the final cured article. In contrast, compositions for inkjet printing processes need to be much lower viscosity to be able to be jetted through nozzles, which is not the case for most vat polymerization resins.

In one embodiment, an orthodontic article is described comprising the reaction product of a polymerizable composition comprising: a) 30-70 parts by weight of monofunctional (meth)acrylate monomer, wherein a cured homopolymer of at least one monofunctional (meth)acrylate monomer has a Tg of at least 30, 35, 40, 45, 50, 55, or 60° C.; and b) urethane (meth)acrylate polymer comprising polymerized units of an aliphatic polyester diol.

In another embodiment, a polymerizable composition is described comprising: a) 30-70 parts by weight of monofunctional (meth)acrylate monomer, wherein a cured homopolymer of at least one monofunctional (meth)acrylate monomer has a Tg of at least 30, 35, 40, 45, 50, 55, 60° C.; and b) urethane (meth)acrylate polymer comprising polymerized units of an aliphatic polyester diol.

In another embodiment, a method of making an article is described comprising: a) providing a photopolymerizable composition, as described herein; b) selectively curing the photopolymerizable composition to form the article; and c) repeating steps a) and b) to form multiple layers and create the article comprising a three-dimensional structure.

In another embodiment, a non-transitory machine-readable medium comprising data representing a three-dimensional model of an article, when accessed by one or more processors interfacing with a 3D printer, causes the 3D printer to create an article comprising a reaction product of a photopolymerizable composition, as described herein.

In another embodiment, a method is described comprising: a) receiving, by a manufacturing device having one or more processors, a digital object comprising data specifying a plurality of layers of an article; and b) generating, with the manufacturing device by an additive manufacturing process, the article based on the digital object, the article comprising a reaction product of a photopolymerizable composition, as described herein.

A system comprising: a) a display that displays a 3D model of an article; and b) one or more processors that, in response to the 3D model selected by a user, cause a 3D printer to create a physical object of an article, the article comprising a reaction product of a photopolymerizable composition, as described herein.

DETAILED DESCRIPTION OF ILLUSTRATIVE EMBODIMENTS

Figure 1:
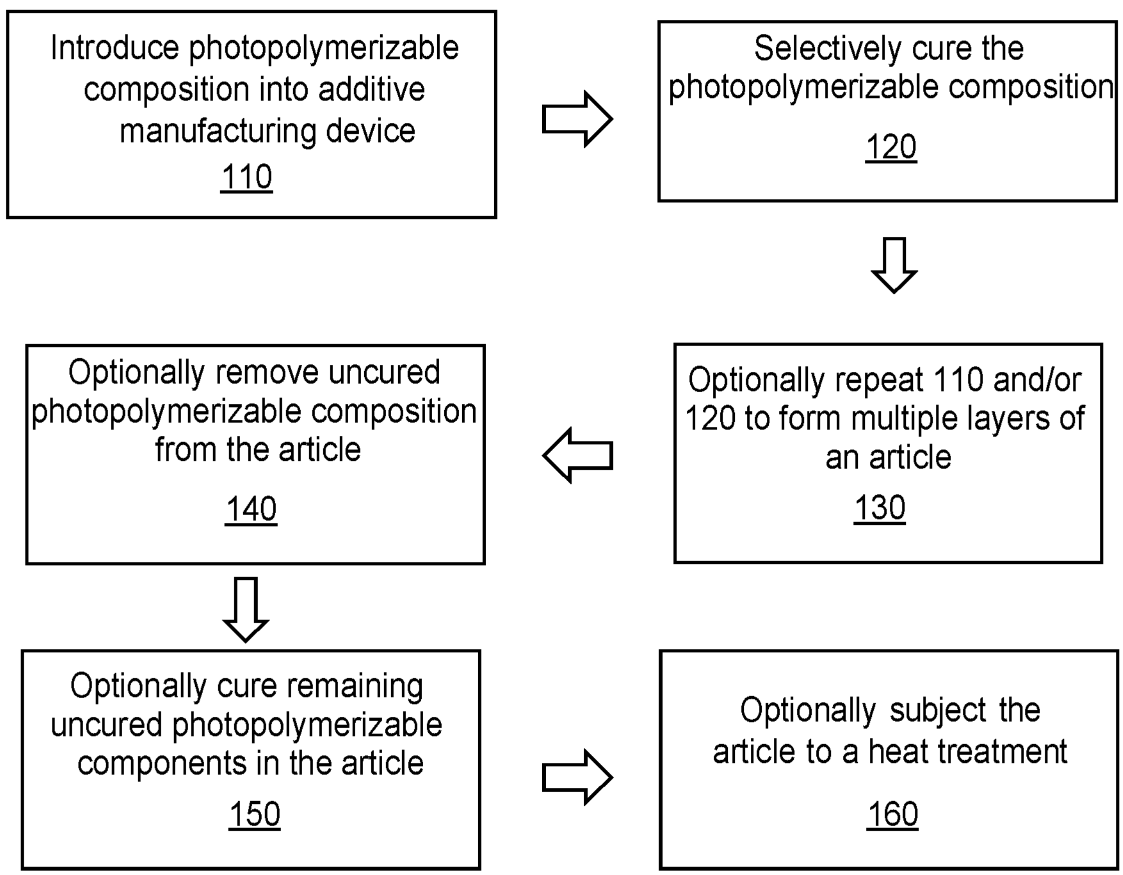
FIG. 1 is a flowchart of a process for building an article using the photopolymerizable compositions disclosed herein.

Presently described are polymerizable compositions and orthodontic articles comprising the reaction product of a polymerizable composition. The polymerizable composition comprises one or more monofunctional (meth)acrylate monomers and one or more polyester urethane (meth)acrylate polymers.

The total amount of monofunctional (meth)acrylate monomer(s) is typically at least 30, 35, or 40 wt. % based on the total weight of the organic components of the composition (e.g. excluding inorganic components, such as filler.) The total amount of monofunctional (meth)acrylate monomer(s) is typically no greater than 70, 65, or 60 wt. %.

The polymerizable composition comprises one or more "high Tg" monofunctional (meth)acrylate monomers, i.e, wherein a cured homopolymer of such monofunctional (meth)acrylate monomer has a Tg of at least 30, 35, 40, 45, 50, 55, 60, 65, 70, 75, 80, 85 or 90° C. In some embodiments, the polymerizable composition comprises at least one of monofunctional (meth)acrylate monomer wherein a cured homopolymer of such monofunctional (meth)acrylate monomer has a Tg of at least 95, 100, 105, 110, 115, 120, 125, 130, 135, 140, 145, 150, 155, 160, 165, 170, 175, 180, 185 or 190° C. The Tg of the homopolymer of the monofunctional (meth)acrylate monomer is typically no greater than about 260° C. For example, 1-adamantyl methacrylate decomposes at about 260° C. In some embodiments, the Tg of the homopolymer of the monofunctional (meth)acrylate monomer is no greater than 255, 250, 245, 240, 235, 230, 225, 220, 215, 210, 205 or 200° C.

Often, the Tg of a homopolymer of a monomer is known from published literature. Table 1 describes the Tg of the homopolymer of various monofunctional (meth)acrylate monomers that may be used in the polymerizable composition of the orthodontic articles described herein. In some embodiments, a single isomer may be used. In other embodiments, a mixture of isomers may be used. Combinations of monofunctional (meth)acrylate monomer(s) can be utilized. In some embodiments, the monofunctional (meth)acrylate monomer is a methacrylate.

In some embodiments, the monofunctional (meth)acrylate monomer comprises a cyclic moiety. Although the cyclic moiety may be aromatic, in typical embodiments, the cyclic moiety is a cycloaliphatic. Suitable monofunctional (meth) acrylate monomers include for instance and without limitation, 3,3,5-trimethylcyclohexyl (meth)acrylate, butyl-cyclohexyl(meth)acrylate, 2-decahydronapthyl (meth)acrylate, 1-adamantyl (meth)acrylate, dicyclopentadienyl (meth)acrylate, bornyl (meth)acrylate including isobornyl (meth)acrylate, dimethyl-1-adamantyl (meth)acrylate, and 3-tetracyclo [4.4.0.1.1]dodecyl methacrylate.

When the polymerized composition contacts an aqueous environment during normal use, such as in the case of orthodontic articles, it is advantageous to utilize materials that have low affinity for water. One way to express the affinity for water of (meth)acrylate monomers is by calculation of the partition coefficient between water and an immiscible solvent, such as octanol. This can serve as a quantitative descriptor of hydrophilicity or lipophilicity. The octanol/water partition coefficient can be calculated by software programs such as ACD ChemSketch, (Advanced Chemistry Development, Inc., Toronto, Canada) using the log P module. In some embodiments, the monofunctional (meth)acrylate monomer has a calculated log P value of greater than 1, 1.5, 2, 2.5, or 3. In some embodiments, the monofunctional (meth)acrylate monomer has a calculated log P value of greater than 3.5, 4, 4.5, or 5. The calculated log P value is typically no greater than 12.5. In some embodiments, the calculated log P value is no greater than 12, 11.5, 11, 10.5, 10, 9.5, 9, 8.5, 8, 7.5, 7, 6.5, 6, or 5.5.

In some embodiments, the polymerizable composition optionally further comprises a monofunctional (meth)acrylate monomer having a high affinity for water, i.e. having a log P value of less than 3, 2.5, 2.0, 1.5, or 1. When present such monomer(s) are present, such monomer(s) having a high affinity for water are typically present in an amount less than the monofunctional (meth)acrylate monomer(s) having a low affinity for water. Thus, the concentration of monofunctional (meth)acrylate monomer(s) having a high affinity for water is typically no greater than 50, 45, 40, 35, 30, or 25 wt. % of the total monofunctional (meth)acrylate monomer(s). In some embodiments, the concentration of monofunctional (meth)acrylate monomer(s) having a high affinity for water is no greater than 24, 23, 22, 21, 20, 19, 18, 17, 16, 15, 14, 13, 12, 11, 10, 9, 8, 7, 6, 5, 4, 3, 2, or 1 wt. % of the total monofunctional (meth)acrylate monomer(s). In other words, the total polymerizable composition typically comprises no greater than 35, 34, 33, 32, 31, 30, 29, 28, 27, 26, 25, 24, 23, 22, 21 or 20 wt. % of reactive diluents(s) (e.g. monofunctional (meth)acrylate monomers) having a high affinity for water. In some embodiments, the total polymerizable composition comprises at least 1, 2, 3, 4, 5, 6, 7, 8, 9, 10, 11, 12, 13, 14, 15, 16, 17, 18, 19, or 20 wt. % of reactive diluents (e.g. (meth)acrylate monomer(s)) having a high affinity for water. In some embodiments, the polymerizable composition comprises an ethylenically unsaturated component with acid functionality as further described in U.S. patent Ser. No. 11/584,817, granted Feb. 21, 2023; inforporated herein by reference. Ethylenically unsaturated components with acid functionality can have a low Log P value and thus a high affinity for water.

TABLE 1

Reported glass transition temperature (Tg) and calculated log P (log of octanol/water partition coefficient) of homopolymers of monofunctional (meth)acrylate monomers.

| Monomer | Tg (° C.) | Tg Reference | Calculated log P |
|---|---|---|---|
| 3,3,5-trimethylcyclohexyl acrylate | 15 | Hopfinger et. al.; J. Polym. Sci. B., Polym. Phys. 1988, 26, 2007 | 4.38 |
| d,l-isobornyl acrylate | 94 | Jakubowski et. al. Polymer, 2008, 49, 1567 | 4.22 |
| dicyclopentanyl acrylate | 103 | U.S. Pat No. 4,591,626 | 3.69 |
| 3,5-dimethyl-1-adamantyl acrylate | 105 | Matsumoto, A. et.al. Macromolecules 1991, 24, 4017 | 4.63 |
| cyclohexyl methacrylate | 107 | Wilson, P.S., Simha, R.; Macromolecules, 1973, 95, 3, 902 | 3.41 |
| tert-butyl methacrylate | 113 | Matsumoto, A. et.al. Macromolecules 1991, 24, 4017 | 2.57 |
| 3,3,5-trimethylcyclohexyl methacrylate | 125 | Hopfinger et. al.; J. Polym. Sci. B., Polym. Phys. 1988, 26, 2007 | 4.93 |
| cis-4-tert-butyl-cyclohexylmethacrylate | 132 | Matsumoto, A. et.al. Macromolecules 1993, 26, 7, 1659 | 5.13 |

TABLE 1-continued

Reported glass transition temperature (Tg) and calculated log P (log of octanol/water partition coefficient) of homopolymers of monofunctional (meth)acrylate monomers.

| Monomer | Tg (° C.) | Tg Reference | Calculated log P |
|---|---|---|---|
| 2-decahydronapthyl methacrylate | 145 | Matsumoto, A. et. al., J. Polym. Sci. A., Polym. Chem. 1993, 31, 2531 | 4.95 |
| 1-adamantyl acrylate | 153 | Matsumoto, A. et.al. Macromolecules 1991, 24, 4017 | 3.68 |
| Mixture of 73% trans-4-tert-butylcyclohexylmethacrylate/27% cis-4-tert-butylcyclohexylmethacrylate | 163 | Matsumoto, A. et.al. Macromolecules 1993, 26, 7, 1659 | 5.13 |
| dicyclopentanyl methacrylate | 173 | US 4,591,626 | 4.24 |
| trans-4-tert-butylcyclohexyl methacrylate | 178 | Matsumoto, A. et.al. Macromolecules 1993, 26, 7, 1659 | 5.13 |
| d,l-isobornyl methacrylate | 191 | Matsumoto, A. et. al., J. Polym. Sci. A., Polym. Chem. 1993, 31, 2531 | 4.77 |
| 3,5-dimethyl-1-adamantyl methacrylate | 194 | Matsumoto, A. et.al. Macromolecules 1991, 24, 4017 | 5.19 |
| d,l-bornyl methacrylate | 194 | Matsumoto, A. et. al., J. Polym. Sci. A., Polym. Chem. 1993, 31, 2531 | 4.77 |
| 3-tetracyclo[4.4.0.1.1]dodecyl methacrylate | 199 | Matsumoto, A. et. al., J. Polym. Sci. A., Polym. Chem. 1993, 31, 2531 | 4.66 |
| 1-adamantyl methacrylate | >253 | Matsumoto, A. et.al. Macromolecules 1991, 24, 4017 | 4.23 |
| 2-ethylhexyl methacrylate | −10 | Fleischhaker et. al., Macromol. Chem. Phys. 2014, 215, 1192. | 4.88 |
| tetrahydrofurfuryl methacrylate | 60 | E.I. du Pont de Nemours & Co., Ind. Eng. Chem., 1936, 28, 1160, | 1.38 |
| 2-phenoxyethyl methacrylate | 47 | Song et. al.; J. Phys. Chem. B 2010, 114, 7172 | 3.26 |
| N-vinyl pyrrolidone | 180 | Turner et. al; Polymer, 1985, 26, 757 | 0.37 |
| carboxyethyl acrylate | <30 | Fang et. al.; Int. J. Adhes. and Adhes. 84 (2018) 387-393 | 0.60 |
| 2-hydroxyethyl methacrylate | 105 | Russell et. al.; J. Polym. Sci. Polym. Phys, 1980, 18, 1271 | 0.50 |
| acryloyl morpholine | 147 | Elles, J.; Chimie Moderne, 1959, 4, 26, 53 | −0.94 |

The selection and concentration of the monofunctional (meth)acrylate monomer(s) contributes to providing a two-phase system wherein the polymerized composition yields and exhibits a sufficient elongation (e.g. at least 15-20%). In typical embodiments, the high Tg monofunctional (meth) acrylate monomer(s) also contributes to improving the 3 point bend modulus at 2% strain. When the Tg of the monofunctional (meth)acrylate monomer(s) is too low, the cured compositions may not have the properties needed to move teeth. When the log P values of the monofunctional (meth)acrylate monomer(s) is too low, the polymerized composition may lose its strength when exposed to aqueous environments. When the amount of high Tg monofunctional (meth)acrylate monomer(s) is too high, the polymerized composition can also be too brittle, failing to yield after soaking in water and exhibiting insufficient elongation.

The polymerizable composition further comprises at least one polyester urethane (meth)acrylate polymer. The polyester urethane (meth)acrylate polymer typically comprises polymerized units of an aliphatic polyester diol.

The polyester urethane (meth)acrylate polymer (e.g. comprising polymerized units of an aliphatic polyester diol) described herein is the primary difunctional (e.g. di(meth) acrylate) component of the polymerizable composition. The total amount of polyester urethane (meth)acrylate polymer is typically at least 30, 35, or 40 wt. % based on the total weight of the organic components of the composition (e.g. excluding inorganic components, such as filler.) The total amount of polyester urethane (meth)acrylate polymer is typically no greater than 70, 65, or 60 wt. %.

In some embodiments, the weight ratio of the monofunctional (meth)acrylate monomer(s) to polyester urethane (meth)acrylate polymer (e.g. comprising polymerized units of an aliphatic polyester diol) can range from 2:1 to 1:2 or 1.5:1 to 1:1.5.

Various polyester urethane (meth)acrylate polymers are commercially available. Other polyester urethane (meth) acrylate polymers can be synthesized.

In typical embodiments, aliphatic polyester diols are utilized in the preparation of the polyester urethane (meth) acrylate polymer.

In some embodiments, the polyester diol has Formula 1, as follows:

$$H[O—R_3—O—C(=O)—R_4—C(=O)]_m—O—R_3—OH$$

wherein $R_3$ and $R_4$ are independently straight or branched chain or cycle-containing alkylene, groups, that optionally include heteroatoms, such as oxygen. $R_3$ and $R_4$ independently comprise 2 to 40 carbon atoms. The subscript "m" is typically at least 2, 3, 4, 5, 6, or 7. The subscript "m" is typically no greater than 50, 45, 40, 35, 30, 25, 20, or 15. In some embodiments, the $R_3$ and $R_4$ are alkylene.

Representative polyester diols include for example neopentyl glycol adipate diol, butane diol adipate diol; 3-methyl-1,5-pentanediol adipate diol; and 3-methyl-1,5-pentanediol sebecate diol, and dimer acid based polyols in which the dimer acid is derived for example from dimerization of two 18 carbon diacids such as linoleic acid.

In some embodiments, such as the diols just described, the polyester diol comprises a single $R_3$ group (e.g. neopentyl or 3-methyl-1,5-pentyl) and a single $R_4$ group (e.g. adipate).

In other embodiments, the aliphatic polyester diol can be prepared from more than one diol and more than one acid. In this embodiment, the diol can contain two or more different $R_3$ groups and two or more different $R_4$ groups such as in the case of ethylene glycol-hexane diol/adipate-azelate copolyester diol.

In other embodiments, the polyester diol has Formula 2, as follows:

$$H[O—R_6—C(=O)]_n—O—R_5—O—[(C(=O)—R_6—O]_o—H.$$

wherein $R_5$ and $R_6$ are independently straight or branched chain or cycle-containing alkylene groups that optionally include heteroatoms such as oxygen, the alkylene groups independently comprise 2 to 40 carbon atoms. The subscripts "n" and "o" (i.e. the letter o) are typically independently at least 4, 5 or 6. The subscripts "n" and "o" are typically independently no greater than 25, 20, or 15.

One representative polyester diol of this type is polycaprolactone diol, such as available from Perstorp. In this embodiment, $R_6$ is a $C_5$ alkylene group and $R_5$ is the residue of an alcohol, such as ethylene glycol, butylene glycol, diethylene glycol, and the like.

In some embodiments, at least one of $R_3$ or $R_4$ of Formula 1 and at least one of $R_5$ and $R_6$ of Formula 2 is a straight or branched chain or cycle-containing alkylene group independently comprising at least 4, 5, or 6 carbon atoms.

In some embodiments, each of the $R_3$ and $R_4$ groups of Formula 1 are alkylene groups independently comprising at least 4, 5, or 6 carbon atoms. In some embodiments, each of the $R_5$ and $R_6$ groups of Formula 2 are alkylene groups independently comprising at least 4, 5, or 6 carbon atoms.

The values of m, n, and o are chosen such that the molecular weight (Mn) of the diol is at least 500, 600, 700, 800, 900, or 1000 g/mole. In some embodiments, the molecular weight (Mn) of the diol is at least 1100, 1200, 1300, 1400, 1500 g/mole. In some embodiments, the molecular weight (Mn) of the diol is at least 1600, 1700, 1800, 1900, or 2000 g/mole. In some embodiments, the molecular weight (Mn) of the diol is no greater than 10,000; 9,000; 8,000; 7,000; 6,000; 5000; 4000; or 3000 g/mole. The molecular weight of the diol can be determined from the —OH value, that can be determined by titration. When the molecular weight is too low the elongation can be insufficient (i.e. less than 15-20%). The values of m, n, and o can vary widely due to the range of carbons for the $R_3$, $R_4$, $R_5$ and $R_6$ groups.

Various hydroxy functional (meth)acrylates can be used in the preparation of the (e.g. polyester) urethane (meth)acrylate polymer. In typical embodiments, the hydroxy functional (meth)acrylate has Formula 3, as follows:

$$HO—Q—(A)p$$

wherein Q is a polyvalent (e.g. divalent or trivalent) organic linking group, A has the formula $—OC(=O)C(R_1)=CH_2$ wherein $R_1$ is H or alkyl of 1 to 4 carbon atoms (e.g. methyl), and p is 1 or 2.

In some embodiments, Q is a straight or branched chain or cycle-containing aliphatic (e.g. divalent) connecting group, such an alkylene. In other embodiments, Q is an aromatic (e.g. divalent) connecting group, such as arylene, aralkylene, and alkarylene. Q can optionally include heteroatoms such as O, N, and S, and combinations thereof. Q can also optionally include a heteroatom-containing functional group such as carbonyl or sulfonyl, and combinations thereof. Q typically comprises no greater than 20 carbon atoms. In some embodiments, A is a methacryl functional group.

In some embodiments, Q is typically alkylene comprising no greater than 12, 10, 8 or 6 carbon atoms. In some embodiments, Q is a $C_2$, $C_3$, or $C_4$ alkylene group. In some embodiments, p is 1. In some embodiments A is methacrylate.

Suitable examples of hydroxy functional (meth)acrylates include for example, 2-hydroxyethyl methacrylate, hydroxypropyl methacrylate (all isomers), hydroxybutyl methacrylate (all isomers), poly(e-caprolactone) mono[2-methacryloxy ethyl] esters, glycerol dimethacrylate, 1-(acryloxy)-3-(methacryloxy)-2-propanol, 2-hydroxy-3-phenyloxypropyl methacrylate, 2-hydroxyalkyl methacryloyl phosphate, 4-hydroxycyclohexyl methacrylate, trimethylolpropane dimethacrylate, trimethylolethane dimethacrylate, 1,4-butanediol monomethacrylate, neopentyl glycol monomethacrylate, 1,6-hexanediol monomethacrylate, 3-chloro-2-hydroxypropyl methacrylate, 2-hydroxy-3-alkyloxymethacrylate, polyethylene glycol monomethacrylate, polypropylene glycol monomethacrylate, —OH terminated ethylene oxide-modified phthalic acid methacrylate, and 4-hydroxycyclohexyl methacrylate.

In some embodiments, a diol (meth)acrylate can be used in the preparation of the urethane (meth)acrylate polymer, such as described in U.S. patent Ser. No. 11/945,900 granted Apr. 22, 2024; incorporated herein by reference. In this embodiment, the urethane (meth)acrylate polymer includes pendent (meth)acrylate groups in addition to terminal (meth) acrylate groups.

Various diisocyanates can be used in the preparation of the urethane (meth)acrylate polymer. In typical embodiments, useful diisocyanates can be characterized by the formula $R_{di}(NCO)_2$, wherein $R_{di}$ is the aliphatic and/or aromatic moiety between the isocyanate groups. Once reacted, $R_{di}$ is also commonly referred to as the residue of the diisocyanate.

Specific examples of suitable diisocyanates include for example 2,6-toluene diisocyanate (TDI), 2,4-toluene diisocyanate, methylenedicyclohexylene-4,4'-diisocyanate (H12MDI), 3-isocyanatomethyl-3,5,5-trimethylcyclohexyl isocyanate (IPDI), 1,6-diisocyanatohexane (HDI), tetramethyl-m-xylylene diisocyanate, a mixture of 2,2,4- and 2,4,4-trimethyl-1,6-diisocyanatohexane (TMXDI), trans-1,4-hydrogenated xylylene diisocyanates (H6XDI), cyclohexyl-1,4-diisocyanate, 4,4'-methylene diphenyl diisocyanate, 2,4'-methylene diphenyl diisocyanate, a mixture of 4,4'-methylene diphenyl diisocyanate and 2,4'-methylene diphenyl diisocyanate, 1,5-naphthalene diisocyanate, 1,4-tetramethylene diisocyanate, 1,4-phenylene diisocyanate, 2,6- and 2,4-toluene diisocyanate, 1,5-naphthylene diisocyanate, 2,4' and 4,4'-diphenylmethane diisocyanate, pentamethylene diisocyanate, dodecamethylene diisocyanate, 1,3-cyclopentane diisocyanate, 1,3-cyclohexane diisocyanate, methyl 2,4-cyclohexane diisocyanate, methyl-2,6-cyclohexane diisocyanate, 1,4-bis(isocyanatomethyl)cyclohexane, 1,3-bis(isocyanatomethyl)cyclohexane, 4,4'-toluidine diisocyanate, 4,4'-diphenyl ether diisocyanate, 1,3- or 1,4-xylylene diisocyanate, lysine diisocyanate methyl ester, 3,3'-dimethyl-4,4'-diphenylmethane diisocyanate, 3,3'-dimethyl-phenylene diisocyanate, 2,5-bis(isocyanate methyl)-bicyclo [2.2.1]heptane, 2,6-bis(isocyanate methyl)-bicyclo[2.2.1] heptane, bis(2-isocyanate ethyl) fumarate, 4-diphenylpropane diisocyanate, trans-cyclohexane-1,4-diisocyanatehydrogenated dimer acid diisocyanate, a norbornene diisocyanate, methylenebis 6-isopropyl-1,3-phenyl diisocyanate, and combinations thereof. In some embodiments, the diisocyanate comprises IPDI.

In one embodied synthetic route, the polyester urethane (meth)acrylate polymer is a reaction product of an aliphatic polyester diol; an (e.g. aliphatic and/or aromatic) diisocyanate, and an (e.g. aliphatic and/or aromatic) hydroxy functional (meth)acrylate.

Such polyester urethane (meth)acrylate polymer can be represented by the following Formula 4:

$$(A)_p—Q—OC(O)NH—R_{di}—NH—C(O)—[O—R_{dOH}—OC(O)NH—R_{di}—NH—C(O)_r]—O—Q—(A)_p$$

wherein, A has the formula —OC(═O)C($R_1$)═$CH_2$ wherein $R_1$ is H or alkyl of 1 (e.g. methyl) to 4 carbon atoms, p is 1 or 2, Q is a polyvalent organic linking group as described above, $R_{di}$ is the residue of a diisocyanate, $R_{dOH}$ is the residue of a polyester polyol, and r averages from 1 to 15. In some embodiments, r is no greater than 15, 14, 13, 12, 11, or 10. In some embodiments, r averages at least 2, 3, 4, or 5. In some embodiments, A is methacrylate.

As evident by such formula, the polyester urethane (meth) acrylate polymer may comprise a central polymerized unit of an aliphatic polyester diol. The aliphatic polyester polymerized unit (derived from the diol) is bonded via urethane linkages formed from one of the isocyanate groups of polymerized units of diisocyanate. The polyester urethane (meth)acrylate polymer comprises terminal groups derived from reaction with a hydroxy functional (meth)acrylate and the opposing isocyanate group of the diisocyanate. When r is 1, the molar ratio of polymerized units of aliphatic polyester diol to polymerized units of diisocyanate is 1:2. When r is a value greater than 1, the molar ratio of polymerized units of aliphatic polyester diol to polymerized units of diisocyanate is 1:greater than 1. For example, when r is 10, the molar ratio of polymerized units of aliphatic polyester diol to polymerized units of diisocyanate is 10:11, or in other words 1:1.1.

One representative reaction product prepared from 2 equivalents of neopentyl glycol adipate based polyester diol, 4 equivalents of isophorone diisocyanate (IPDI), and 2 equivalents of hydroxyl ethyl methacrylate is as follows:

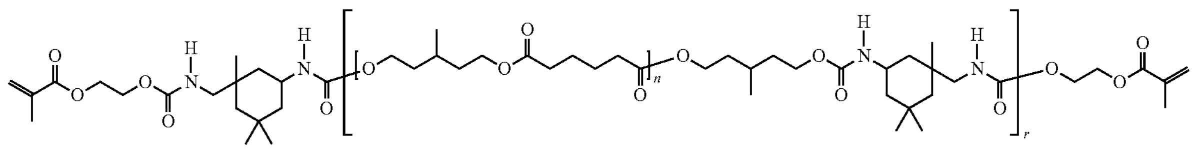

Although the reaction product can have a mixture of polyester urethane (meth)acrylate polymers, wherein r ranges from 1-10 as described above, in some embodiments, the major polyester urethane (meth)acrylate polymer of the above formulas is wherein r=1.

In another embodied synthetic route, the polyester urethane (meth)acrylate polymer is a reaction product of an aliphatic polyester diol, as described above, and an (e.g. aliphatic and/or aromatic) isocyanate functional (meth)acrylate, typically in the presence of a catalyst.

In typical embodiments, the isocyanate functional (meth) acrylate has Formula 5 as follows:

$$(A)_p—Q—NCO$$

wherein A and Q are the same as described above with respect to the hydroxyl functional (meth)acrylate.

Examples of the isocyanate functional (meth)acrylates include isocyanatoethyl methacrylate, isocyanatoethoxyethyl methacrylate, isocyanatoethyl acrylate, and 1,1-(bisacryloyloxymethyl) ethyl isocyanate, which are for instance commercially available from Showa Denko (Tokyo, Japan).

Such polyester urethane (meth)acrylate polymers can be represented by the following Formula 6:

$$(A)_p—Q—NHC(O)O—R_{dOH}—OC(O)NH—Q—(A)_p$$

wherein A, p, Q and $R_{dOH}$ are the same as described above. In some embodiments, A is methacrylate.

One representative reaction product prepared from neopentyl glycol adipate based polyester diol and isocyanatoethyl methacrylate is as follows:

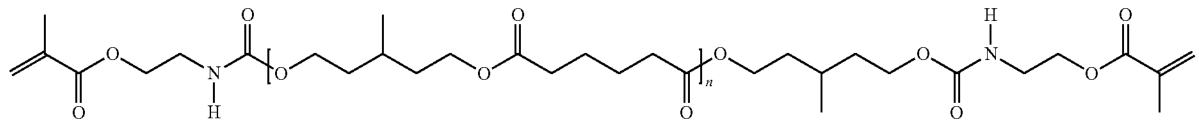

As evident by such formula, the polyester urethane (meth) acrylate polymer may comprise a central polymerized unit of an aliphatic polyester diol. The aliphatic polyester polymerized unit (derived from the diol) is bonded via a urethane linkage to a (meth)acrylate terminal group. This class of polyester urethane (meth)acrylate polymers lacks polymerized diisocyanate moieties. The molar ratio of polymerized units of aliphatic polyester diol to polymerized units of isocyanate functional (meth)acrylate is 1:2.

In the preparation of the polyester urethane (meth)acrylate polymer the equivalence of isocyanate groups (diisocyanate or isocyanate functional (meth)acrylate) is about equal to the equivalence of hydroxyl groups of the aliphatic polyester diol and hydroxyl functional (meth)acrylate. Typically, the aliphatic polyester diol and/or hydroxyl functional (meth) acrylate are present such that there is a slight excess of hydroxyl groups resulting in substantially all the isocyanate groups being consumed during the polymerization.

In some embodiments, the equivalence of diisocyanate is greater than the equivalence of aliphatic polyester diol. In some embodiments, the equivalent ratio of diisocyanate to aliphatic polyester diol is at least 1.1:1, 1.2:1, or 1.3:1 ranging up to 1.5:1, 2:1, 2.5:1, 3:1, 3.5:1, 4.1, 4.5:1 or 5:1.

The equivalent ratio of the aliphatic polyester diol to the hydroxyl functional (meth)acrylate can range from 4:1 to 1:4, 3.5:1 to 1:3.5 or 3:1 to 1:3. When the equivalent ratio of the aliphatic polyester diol to the hydroxyl functional (meth)acrylate is 1:1 or greater than 1:1 (e.g. 1.5:1, 2:1, 2.5:1 or 3:1, the formula depicted above is the major reaction product (e.g. at least 94, 95, 96, 97, 98, or 99% of the total reaction products). In this embodiment, the equivalence of aliphatic polyester diol is equal to or greater than the equivalence of hydroxyl functional (meth)acrylate. In other embodiments, the equivalence of the hydroxyl functional (meth)acrylate is greater than the equivalence of the aliphatic polyester diol. When the equivalent ratio of aliphatic polyester diol to the hydroxyl functional (meth)acrylate at least 1:1.2, 1:1.3, 1:1.3, 1:1.4, 1.1.5, 1.16, or greater; increasing concentrations of the reaction product of the diisocyanate with only the hydroxyl functional (meth)acrylate (at the exclusion of the diol) can be produced as a by-product. The selection of diisocyanate can also result in higher concentrations of by-product. For example, when hydrogenated methylene diisocyanate (H12MDI) is utilized instead of isophorone diisocyanate (IPDI), higher concentrations of byproduct are produced. Additionally, for materials made at the same ratio of diisocyanate:diol:hydroxyl functional (meth)acrylate, materials made with higher molecular weight diols have lower weight percentages of the by-product than materials made with lower with lower molecular weight diols.

In some embodiments, the urethane (meth)acrylate polymer is prepared from a (e.g. aliphatic) polyester diol as described above and a second diol that is not a (e.g. aliphatic) polyester diol. The second diol may be for example an aromatic polyester diol, a polycarbonate diol, a polyalkylene oxide diol, or combination thereof.

The wt-% of aliphatic polyester diol is typically greater than or equal to the wt. % of aromatic polyester diol. In some embodiments, the weight ratio of aliphatic polyester diol(s) to aromatic polyester diol(s) ranges from 1:1 to 10:1. In some embodiments, the weight ratio of aliphatic polyester diol(s) to aromatic polyester diol(s) is at least 2:1, 3:1, 4:1, 5:1, 6:1, 7:1, 8:1, or 9:1.

The wt-% of (e.g. aliphatic) polyester diol is typically greater than or equal to the wt. % of second diol that is not a polyester diol. In some embodiments, the weight ratio of polyester diol to second diol(s) (e.g. polyalkylene oxide and/or polycarbonate diol) ranges from 1:1 to 10:1. In some embodiments, the weight ratio of polyester diol to second diol(s) is at least 2:1, 3:1, 4:1, 5:1, 6:1, 7:1, 8:1, or 9:1. In some embodiments, the wt. % of polyalkylene oxide (e.g. especially polyethylene oxide) moieties is no greater than 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 wt.-% of the polymerizable resin. Thus, the urethane (meth)acrylate polymer can comprise polymerized units derived from a polyester diol and second diol at the amounts just described.

The polyester urethane (meth)acrylate polymer typically has a number average molecular weight (Mn) of at least 500 g/mol and in some embodiments at least 750 g/mol, 1,000 g/mol, 1,250 g/mol, 1500 g/mol, 1,750 g/mol or 2,000 g/mol. In some embodiments, the polyester urethane methacrylate polymer has a number average molecular weight (Mn) of at least 2,500 g/mol, 3,000 g/mol, 3,500 g/mol, 4,000 g/mol, 4,500 g/mol, 5,000 g/mol, 5,500 g/mol or 6,000 g/mol. The polyester urethane (meth)acrylate polymer typically has a number average molecular weight (Mn) no greater than 25,000 g/mol. In some embodiments, the polyester urethane (meth)acrylate polymer has a number average molecular weight (Mn) of no greater than 20,000 g/mol, 15,000 g/mol or 10,000 g/mol.

The polyester urethane (meth)acrylate polymer typically has a weight average molecular weight (Mw) of at least 2000 g/mol and in some embodiments at least 2,500 g/mol, 3,000 g/mol, or 3500 g/mol. In some embodiments, the polyester urethane methacrylate polymer has a weight average molecular weight (Mw) of at least 4,000 g/mol, 5,000 g/mol, 6,000 g/mol, 7,000 g/mol, 8,000 g/mol, 9,000 g/mol, or 10,000 g/mol. The polyester urethane (meth)acrylate polymer typically has a weight average molecular weight (Mw) no greater than 50,000 g/mol, 45,000 g/mol, 40,000 g/mol, 35,000 g/mol, or 30,000 g/mol. Higher molecular weight urethane (meth)acrylates will result in higher viscosity resin formulations with comparable compositions and concentrations, that increase the viscosity. When the molecular weight is too low, the cured composition can fail to yield and/or exhibit insufficient elongation (i.e. less than 15-20%). The lower molecular weight polyester urethane (meth)acrylate polymers may be characterized as oligomers.

Molecular weight (Mw and Mn) of the urethane (meth) acrylate polymer is determined by GPC as described in the example section.

In some embodiments, the polymerizable composition further comprises other difunctional (e.g. di(meth)acrylate) components.

In some embodiments, the composition further comprises a difunctional (e.g. di(meth)acrylate) (e.g. by-product) component that is the reaction product of the same diisocyanate and same hydroxy functional (meth)acrylate as that of the polyester urethane (meth)acrylate polymer.

Such polyurethane (meth)acrylate can be represented by the following Formula 7:

$$(A)_p—Q—OC({=}O)NH—R_{di}—NHC({=}O)O—Q—(A)_p$$

wherein A, Q, and p, are the same as previously described for the hydroxy functional (meth)acrylate and $R_{di}$ is a residue of a diisocyanate as previously described. In some embodiments, A is methacrylate.

When the hydroxyl functional (meth)acrylate is HEMA and the diisocyanate is IPDI, the polyurethane (meth)acrylate has the following formula:

canediol dimethacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate, or any combination thereof. Further suitable difunctional monomers include the di(meth)acrylates of each of the above listed diacrylates.

The total amount of other difunctional (e.g. di(meth) acrylate) components (including by-product) can be at least

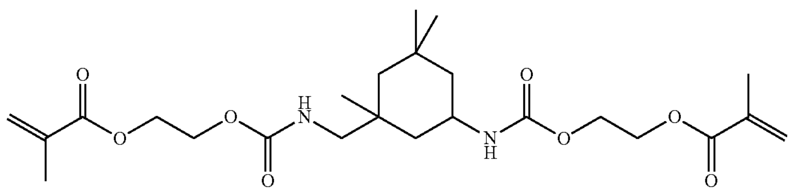 [SMILES: C=C(C)C(=O)OCCOC(=O)NCC1(C)CC(NC(=O)OCCOC(=O)C(=C)C)CC(C)(C)C1]

The amount of polyurethane (meth)acrylate lacking polyester moieties (e.g. by-product) that is formed during the polymerization can vary. In some embodiments, polyurethane (meth)acrylate lacking polyester moieties (e.g. by-product) is present in amounts less than 3, 2, or 1 wt. % based on the total weight of the polymerizable organic components of the composition.

The presence of such polyurethane (meth)acrylate lacking polyester moieties may advantageously improve crosslinking thereby increasing the modulus of the photopolymerized reaction product. In view of such benefits, such polyurethane (meth)acrylate lacking polyester moieties can be prepared separately and be added to the polymerizable composition if desired, in addition to being present as a reaction by-product.

The polymerizable compositions may optionally include other difunctional (meth)acrylate monomer(s) or polymer(s). The other difunctional (meth)acrylate monomer(s) or polymer(s) may include the reaction product of diisocyanates and hydroxy functional (meth)acrylates as previously described that were not utilized in the preparation of the polyester urethane (meth)acrylate polymer.

The optional difunctional (e.g. di(meth)acrylate) monomer(s) or polymer(s) can include other urethane (meth) acrylate polymers, such as urethane (meth)acrylate polymers that comprise aromatic (e.g. polyester) moieties. The optional difunctional (e.g. di(meth)acrylate) monomer(s) or polymer(s) can include urethane (meth)acrylate polymers that lack polyester moieties, such as urethane (meth)acrylate polymers that comprise polyether moieties or urethane (meth)acrylate polymers that comprise polycarbonate moieties. The other difunctional (e.g. di(meth)acrylate) monomer(s) or polymer(s) can include (e.g. polyester) urethane (meth)acrylate polymers having a lower molecular weight.

The optional difunctional (e.g. di(meth)acrylate) monomer(s) or polymer(s) can include other di(meth)acrylate monomers that lack urethane moieties, such as 1,12-dode- 0.5, 1, 2, 3, 4, or 5 wt. % based on the total weight of the polymerizable organic components of the composition. In some embodiments, the total amount difunctional (e.g. di(meth)acrylate) components (including by-product) is no greater than 20, 19, 18, 17, 16, or 15 wt. %. In some embodiments, the total amount difunctional (e.g. di(meth) acrylate) components including by-product) is no greater than 14, 13, 12, 11, or 10 wt. %.

The polyester urethane (meth)acrylate is the major urethane (meth)acrylate polymer. When other urethane (meth) acrylate polymers and/or or difunctional (e.g. di(meth)acrylate) components are present, the weight ratio of polyester urethane (meth)acrylate to the total of other urethane (meth) acrylate polymers and/or or difunctional (e.g. di(meth)acrylate) components typically ranges from 1:1 to 25:1. In some embodiments, the weight ratio of polyester urethane (meth) acrylate to the total of other urethane (meth)acrylate polymers and/or or difunctional (e.g. di(meth)acrylate) components is at least 2:1, 3:1, or 4:1.

In favored embodiments, the polyester urethane (meth) acrylate polymer has a low affinity for water. In this embodiment, the polyester urethane (meth)acrylate polymer comprises little or no oxygen-containing moieties that are not polyester moieties or (meth)acrylate moieties. For example, the polyester urethane (meth)acrylate comprises little or no polyether moieties such as polyethylene oxide moieties. Further, the urethane (meth)acrylate comprises little or no pendent hydroxyl moieties.

When the composition further comprises other difunctional (e.g. di(meth)acrylate) monomer(s) or polymer(s), such as described above, the other difunctional (e.g. di(meth)acrylate) components also have a low affinity for water as just described. Alternatively, the other difunctional (e.g. di(meth)acrylate) components have a higher affinity for water but are utilized at sufficiently low concentrations as to not detract from the desired properties (e.g. strength at yield, elongation at break, and bend modulus; as will subsequently be described. For example, the amount of polyethylene oxide moieties (e.g. of the polyol or additional polymer) is typically no greater than 20 wt. % based on the total weight of the composition.

Photoinitiator

Photopolymerizable compositions of the present disclosure include at least one photoinitiator. Suitable exemplary photoinitiators are those available under the trade designations OMNIRAD from IGM Resins (Waalwijk, The Netherlands) and include 1-hydroxycyclohexyl phenyl ketone (OMNIRAD 184), 2,2-dimethoxy-1,2-diphenylethan-1-one (OMNIRAD 651), bis(2,4,6 trimethylbenzoyl)phenylphosphineoxide (OMNIRAD 819), 1-[4-(2-hydroxyethoxy)phenyl]-2-hydroxy-2-methyl-1-propane-1-one (OMNIRAD 2959), 2-benzyl-2-dimethylamino-1-(4-morpholinophenyl) butanone (OMNIRAD 369), 2-Dimethylamino-2-(4-methyl-benzyl)-1-(4-morpholin-4-yl-phenyl)-butan-1-one (OMNIRAD 379), 2-methyl-1-[4-(methylthio)phenyl]-2-morpholinopropan-1-one (OMNIRAD 907), Oligo[2-hydroxy-2-methyl-1-[4-(1-methylvinyl)phenyl]propanone] ESACURE ONE (Lamberti S.p.A., Gallarate, Italy), 2-hydroxy-2-methyl-1-phenyl propan-1-one (DAROCUR 1173), 2,4,6-trimethylbenzoyldiphenylphosphine oxide (OMNIRAD TPO), and 2,4,6-trimethylbenzoylphenyl phosphinate (OMNIRAD TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

In some embodiments, a photoinitiator is present in a photopolymerizable composition in an amount of up to about 5% by weight, based on the total weight of polymerizable components in the photopolymerizable composition. In some embodiments, a photoinitiator is present in an amount of 0.1, 0.2, 0.3, 0.4, 0.5, 0.6, 0.7, 0.8, 0.9, or 1.0 wt. %, based on the total weight of the polymerizable organic components of the composition. In some embodiments, a photoinitiator is present in an amount of at least 1.25 or 1.5 wt. %. The amount of photoinitiator is typically no greater than 5, 4.5, 4, 3.5, 3, 2.5 or 2 wt. %.

Further, a thermal initiator can optionally be present in a photopolymerizable composition described herein. In some embodiments, a thermal initiator is present in a photopolymerizable composition or in an amount of up to about 5% by weight, based on the total weight of polymerizable components in the photopolymerizable composition. In some cases, a thermal initiator is present in an amount of about 0.1-5% by weight, based on the total weight of polymerizable components in the photopolymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, DE) under the VAZO trade designation including VAZO 67 (2,2'-azo-bis(2-methybutyronitrile)) VAZO 64 (2,2'-azo-bis(isobutyronitrile)) and VAZO 52 (2,2'-azo-bis(2,2-dimethyvaleronitrile)), and LUCIDOL 70 from Elf Atochem North America, Philadelphia, PA.

In some embodiments, the use of more than one initiator assists in increasing the percentage of monomer that gets incorporated into the reaction product of polymerizable components and thus decreasing the percentage of the monomer that remains uncured.

In some embodiments, the photoinitiator may be polymeric or a macromolecule, as described in U.S. Patent Application 62/769,375 filed Nov. 19, 2018. In other embodiments, a first photoinitiator and a second free-radical initiator are utilized. The second free-radical initiator is a thermal initiator or a photoinitator having sufficient absorbance at a different wavelength range than the first photoinitiator. Such combination of photoinitiators is described in U.S. Patent Application 62/769,305 filed Nov. 19, 2018; incorporated herein by reference.

Catalyst

The polymerizable composition typically comprises a catalyst. The amount of catalyst is typically 0.01 wt. % to 5 wt. %, based on the total weight of the polymerizable organic components.

Examples of suitable catalysts include for example, dioctyl dilaurate (DOTDL), stannous octoate, dibutyltin diacetate, dibutyltin dilaurate, dibutyltin mercaptide, dibutyltin thiocarboxylate, dibutyltin dimaleate, dioctyltin mercaptide, dioctyltin thiocarboxylate, lead 2-ethylhexanoate, tetra-alkyl titanates such as tetrabutyl titanate (TBT), triethylamine, N,N-dimethylcyclohexylamine, N-methylmorpholine, N-ethylmorpholine, N,N-dimethyl-p-toluidine, beta-(dimethylamino) propionitrile, N-methylpyrrolidone, N,N-dicyclohexylmethylamine, dimethylaminoethanol, dimethylamino-ethoxyethanol, triethylenediamine, N,N,N'-trimethyl aminoethyl ethanol amine, N,N,N',N'-tetramethylethylenediamine, N,N,N',N'-tetramethyl-1,3-diamine, N,N,N',N'-tetramethyl-1,6-hexanediol-diamine, bis(N,N-dimethylaminoethyl) ether, N'-cyclohexyl-N,N-dimethyl-formamidine, N,N'-dimethylpiperazine, trimethyl piperazine, bis(aminopropyl) piperazine, N—(N,N'-dimethylaminoethyl) morpholine, bis(morpholinoethyl) ether, 1,2-dimethyl imidazole, N-methylimidazole, 1,4-diamidines, diazabicyclo-[2.2.2]-octane (DABCO), 1,4-diazabicyclo[3.3.0]-oct-4-ene (DBN), 1,8-diazabicyclo-[4.3.0]-non-5-ene (DBN), 1,8-diazabicyclo-[5.4.0]-undec-7-ene (DBU), and phenol salts, salts such as octyl acid salts, N,N, N',N"-pentamethyldiethylenetriamine, N,N,N',N"-pentamethyl dipropylenetriamine, tetramethylguanidine, N-cyclohexyl-N',N',N",N"-tetramethyl guanidine, N-methyl-N'-(2-dimethyl amino ethyl) piperazine, 1,3,5-tris (N,N-dimethyl-propyl)-hexahydro-1,3,5-triazine.

In some embodiments, the catalyst comprises zinc, an amine, tin, zirconium, or bismuth. The catalyst can comprise tin, such as dibutyltin diacrylate. Preferably, however, the catalyst is free of tin, as tin catalysts may not be desirable to include in orthodontic articles that will be in contact with a patient's mouth.

The catalyst may comprise an organometallic zinc complex that is free of 2-ethylhexyl carboxylate and 2-ethylhexanoic acid, such as the zinc catalyst commercially available from King Industries, Inc. (Norwalk, CT) under the trade designation K-KAT XK-672, and/or other zinc catalysts available from King Industries, such as K-KAT XK-661, and K-KAT XK-635. Another suitable catalyst is bismuth neodecanoate, for instance commercially available from Sigma-Aldrich (St. Louis, MO), as well as bismuth catalysts available from King Industries under the trade designations K-KAT XK-651 and K-KAT 348. Available aluminum based catalysts include K-KAT 5218 from King Industries. Further, zirconium based catalysts include K-KAT 4205 and K-KAT 6212 available from King Industries.

Additives

Polymerizable compositions described herein typically further comprise one or more additives, such as inhibitors, stabilizing agents, sensitizers, absorption modifiers, fillers and combinations thereof.

In addition, a photopolymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the photopolymerizable composition, a sensitizer can be present in an amount ranging of about 0.01% by weight or about 1% by weight, based on the total weight of the photopolymerizable composition.

A photopolymerizable composition described herein optionally also comprises one or more polymerization inhibitors or stabilizing agents. A polymerization inhibitor is often included in a photopolymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the photopolymerizable composition. Further, if used, a stabilizing agent is present in a photopolymerizable composition described herein in an amount of about 0.1-5% by weight, about 0.5-4% by weight, or about 1-3% by weight, based on the total weight of the photopolymerizable composition.

A photopolymerizable composition as described herein can also comprise one or more UV absorbers including dyes, optical brighteners, pigments, particulate fillers, etc., to control the penetration depth of actinic radiation. One particularly suitable UV absorber include Tinuvin 326 (2-(5-chloro-2H-benzotriazol-2-yl)-6-(1,1-dimethylethyl)-4-methylphenol, obtained from BASF Corporation, Florham Park, NJ. Another particularly suitable absorption modifier is Tinopal OB, a benzoxazole, 2,2'-(2,5-thiophenediyl)bis[5-(1,1-dimethylethyl)], also available from BASF Corporation. Another suitable UV absorber is an optical brightener comprising the following compound

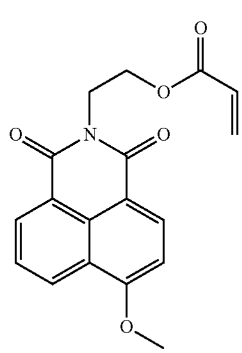 [SMILES: C=CC(=O)OCCN1C(=O)c2cccc3c(OC)ccc(c23)C1=O]

The UV absorber, if used, can be present in an amount of about 0.001-5% by weight, about 0.01-1% by weight, about 0.1-3% by weight, or about 0.1-1% by weight, based on the total weight of the photopolymerizable composition.

Photopolymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, OH and CAB-O-SIL M5 and TS-720 silica from Cabot Corp., Tuscola, IL). Organic fillers made from polymeric materials are also possible, such as those disclosed in International Publication No. WO09/045752 (Kalgutkar et al.).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, MN). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, MN), such as NEXTEL 312, 440, 610 and 720. One presently preferred ceramic fiber comprises polycrystalline $\alpha$-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, MN). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, MN). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the photopolymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Photopolymerizable compositions materials herein can also exhibit a variety of desirable properties, non-cured, cured, and as post-cured articles. A photopolymerizable composition, when non-cured, has a viscosity profile consistent with the requirements and parameters of one or more additive manufacturing devices (e.g., 3D printing systems). Advantageously, in many embodiments the photopolymerizable composition contains a minimal amount of (e.g. organic) solvent. For example, the composition may comprise 95% to 100% solids, preferably 100% solids or in other words no greater than 5, 4, 3, 2, 1, or 0.5 wt. % (e.g. organic solvent). In some embodiment, polymerizable and photopolymerizable compositions are described characterized by a dynamic viscosity of about 0.1-1,000 Pa·s, about 0.1-100 Pa·s, or about 1-10 Pa·s using a TA Instruments AR-G2 magnetic bearing rheometer using a 40 mm cone and plate measuring system at 40 degrees Celsius and at a shear rate of 0.1 1/s. In some embodiments, the composition exhibits a dynamic viscosity of less than about 10 Pa·s.

The polymerizable and photopolymerizable compositions described herein are suitable for making various articles, particularly orthodontic articles are described in further detail below.

The shape of the article is not limited, and may comprise a film or a shaped integral article. For instance, a film may readily be prepared by casting the photopolymerizable composition described herein, then subjecting the cast composition to actinic radiation to polymerize the photopolymerizable composition. In many embodiments, the article comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods.

The conformability and durability of a cured article made from the photopolymerizable compositions of the present disclosure can be determined in part by standard tensile, modulus, and/or elongation testing. The photopolymerizable compositions can typically be characterized by at least one of the following parameters after hardening.

The cured (i.e. polymerized) composition (or orthodontic article prepared from such article) is of sufficient strength and flexibility such that the cured composition yields. When the composition is too brittle, the cured composition does not yield and exhibits low elongation at break. When the composition is not of sufficient strength, rectangular specimens of the cured composition cannot be clamped in order to conduct the 3-point bend modulus test using dynamic mechanical analysis or the 3-point bend modulus is too low, (e.g. less than 100 MPa).

In typical embodiments, the tensile strength of the cured composition at yield of at least 10, 11, 12, 13, or 14 MPa as determined, as determined according to ASTM-D638-14, using test specimen V, after conditioning (i.e., soaking) of a sample of the material of the orthodontic article in phosphate-buffered saline having a pH of 7.4, for 24 hours at a temperature of 37° C. ("PBS Conditioning"). High tensile strength contributes to the article having sufficient strength to be resilient during use in a patient's mouth. Preferably, an article exhibits a tensile strength at yield of 15 MPa or greater, 17 MPa or greater, 20 MPa or greater, 25 MPa or greater, 30 MPa or greater, 35 MPa or greater. In some embodiments, the tensile yield strength is not greater than about 55 MPa.

The cured composition (or orthodontic article prepared from such composition) typically exhibits an elongation at of at least 15, 16, 17, 18%, 19% or 20%, using the same method as just described for the tensile yield strength. In some embodiments, the cured composition exhibits an elongation at break of 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 100% or greater, 110% or greater, or even 120% or greater. In some embodiments, the elongation is no greater than about 500, 400, 300, or 200%.

The cured composition (or orthodontic article prepared from such article) typically exhibits a 3-point bend modulus of at least 100 megapascals (MPa) as determined according to the dynamic mechanical analysis 3-point bend test at 2% strain after conditioning in deionized water for 48 hours at room temperature (i.e., 22 to 25° C.) Preferably, the cured composition exhibits a 3-point bend modulus of 200 MPa or greater, 300 MPa or greater, 400 MPa or greater, 500 MPa or greater, 600 MPa or greater, 700 MPa or greater, 800 MPa or greater, 900 MPa or greater, 1,000 MPa or greater, 1,100 MPa or greater, or even 1,200 MPa or greater. In some embodiments, the 3-point bend modulus is no greater than about 3000, 2500, 2000, or 1500 MPas.

The cured polymerizable composition (or orthodontic article prepared from such article) typically exhibit a first phase have a peak loss modulus temperature of less than 0, −5, or −10° C. and a second phase have a peak tan delta temperature of greater than 30, 40, 50, 60, 70, or 80° C. In some embodiments, the peak loss modulus temperature is at least −70, −65, −60, −55, or −50° C. In some embodiments, the peak tan delta temperature is no greater than 150, 145, 140, 135, or 130° C.

The peak loss modulus and peak tan delta temperatures can be determined according to the dynamic mechanical analysis test method described in the examples. The term peak does not necessarily mean the global maximum value in loss modulus, but can be a local maximum value, or a should on a larger peak. Loss modulus and tan delta are explained, for instance, in Sepe, M. P. (1998 Dynamic Mechanical Analysis for Plastics Engineering. William Andrew Publishing/Plastics Design Library).

In certain embodiments, an article comprises 2 wt. % or less extractable components, 1 wt. % or less, 0.75 wt. % or less, 0.5 wt. % or less, or even 0.1% or less extractable components, based on the total weight of the article. Either an organic (e.g. hexane) solvent or water can be used to extract component. Post-processing of the article to assist in achieving a low concentration of extractables.

The above mechanical properties are particularly well suited for orthodontic articles, for example, that require resiliency and flexibility, along with adequate wear strength and low hygroscopicity.

Methods

In another embodiment, a method of making an (e.g. orthodontic aligner) article is described. The method includes a) providing a photopolymerizable composition as described herein; and b) polymerizing the photopolymerizable composition.

The components are as discussed in detail above. In many embodiments, the photopolymerizable composition of the article is vat polymerized, as discussed in detail below. Optionally, when formed using additive manufacturing methods, the article comprises a plurality of layers.

Photopolymerizable compositions described herein can be mixed by known techniques. In some embodiments, for instance, a method for the preparation of a photopolymerizable composition described herein comprises the steps of mixing all or substantially all of the components of the photopolymerizable composition, heating the mixture, and optionally filtering the heated mixture. Softening the mixture, in some embodiments, is carried out at a temperature of about 50° C. or in a range from about 50° C. to about 85° C. In some embodiments, a photopolymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

In many embodiments, the photopolymerizable composition is vat polymerized, as discussed in detail below.

The shape of the article is not limited, and typically comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods. Specific orthodontic articles are described in further detail below.

In many embodiments, the photopolymerizable composition is cured using actinic radiation comprising UV radiation, e-beam radiation, visible radiation, or a combination thereof. Moreover, the method optionally further comprises post curing the article using actinic radiation or heat.

In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall.

A photopolymerizable composition described herein in a cured state, in some embodiments, can exhibit one or more desired properties. A photopolymerizable composition in a "cured" state can comprise a photopolymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured photopolymerizable composition is at least about 50%, at least about 70%, at least about 80%, or at least about 90% polymerized or crosslinked. A cured photopolymerizable composition can also be between about 10% and about 99% polymerized or crosslinked.

Fabricating an Article

Once prepared as set forth above, the photopolymerizable compositions of the present disclosure may be used in myriad additive manufacturing processes to create a variety of articles, including casting a film or article. A generalized method 100 for creating three-dimensional articles is illustrated in FIG. 1. Each step in the method will be discussed in greater detail below. First, in Step 110 the desired photopolymerizable composition (e.g., comprising a monofunctional (meth)acrylate monomer and polyurethane (meth) acrylate polymer) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three-dimensional structure (e.g., a tensile bar). Optionally uncured photopolymerizable composition is removed from the article in Step 140; further optionally, the article is subjected to additional curing to polymerize remaining uncured photopolymerizable components in the article in Step 150; and still further optionally, the article is subjected to heat treatment in Step 160.

Methods of printing a three-dimensional article or object described herein can include forming the article from a plurality of layers of a photopolymerizable composition described herein in a layer-by-layer manner. Further, the layers of a build material composition can be deposited according to an image of the three-dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, SC and the Asiga PICO PLUS 39, available from Asiga USA, Anaheim Hills, CA.

Figure 2:
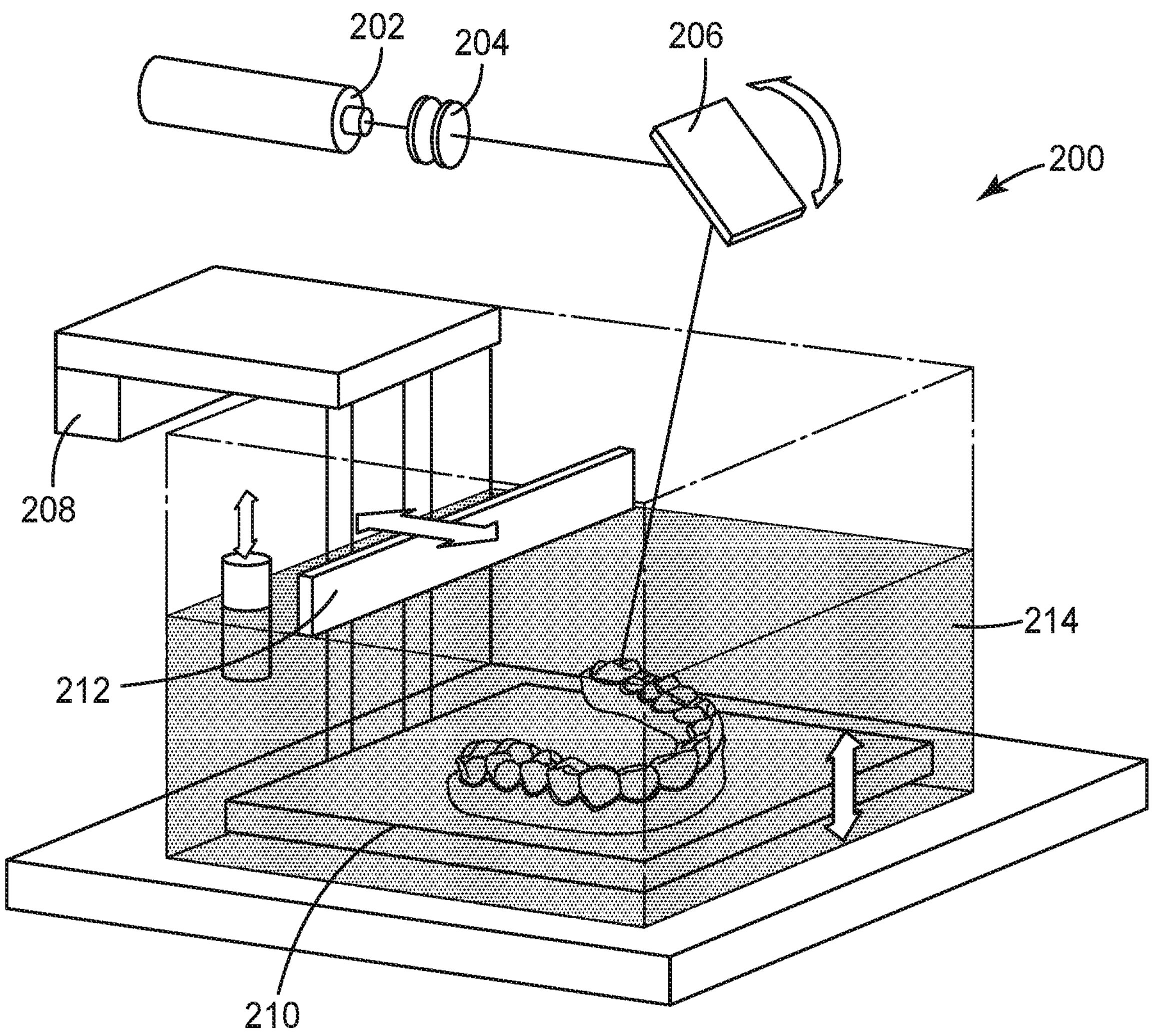
FIG. 2 is a generalized schematic of a stereolithography apparatus.
Figure 3:
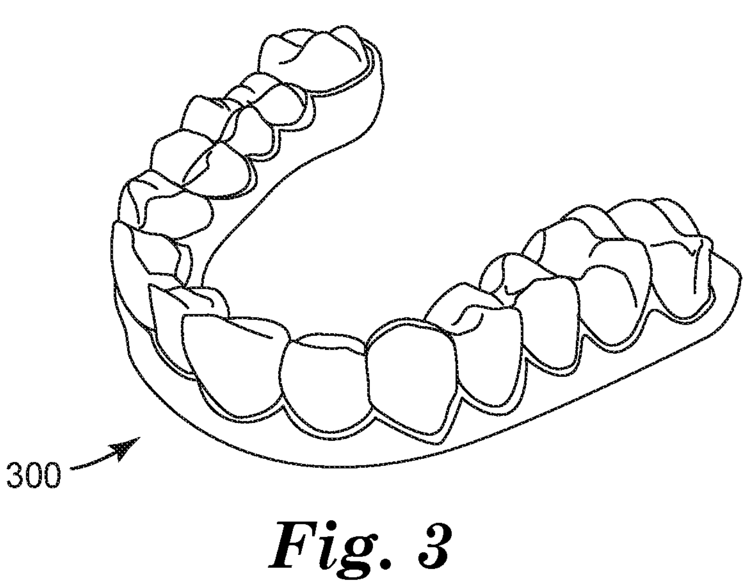
FIG. 3 is an isometric view of a printed clear tray aligner, according to one embodiment of the present disclosure.
Figure 4:
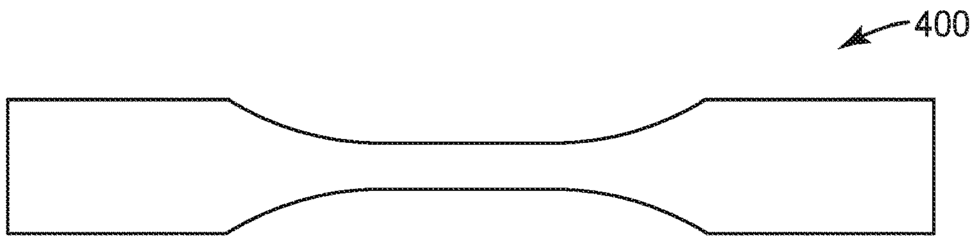
FIG. 4 is an isometric view of a printed tensile bar, according to one embodiment of the present disclosure.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, CA), for instance as described in U.S. Pat. Nos. 9,205,601 and 9,360,757 (both to DeSimone et al.).

Figure 5:
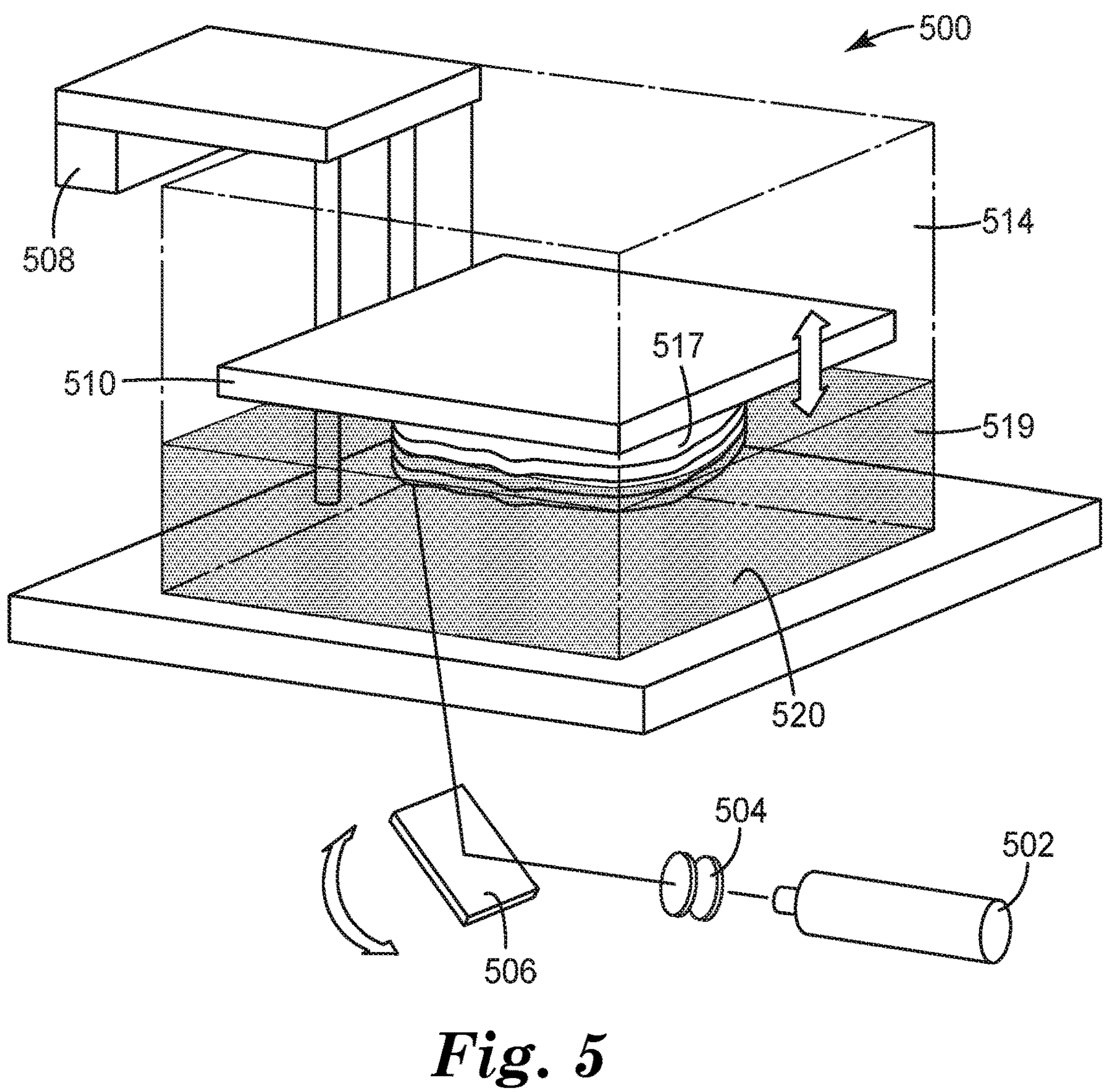
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional post curing. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to post curing.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be post cured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure process of Step 150 and/or Step 160. In general, post curing improves the mechanical properties and stability of the three-dimensional article relative to the same three-dimensional article that is not post cured.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

Various dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to, crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition as described herein.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In embodiments wherein the article is an orthodontic article, scanning techniques may include, for example, scanning a patient's mouth to customize an orthodontic article for the patient.

Figure 10:
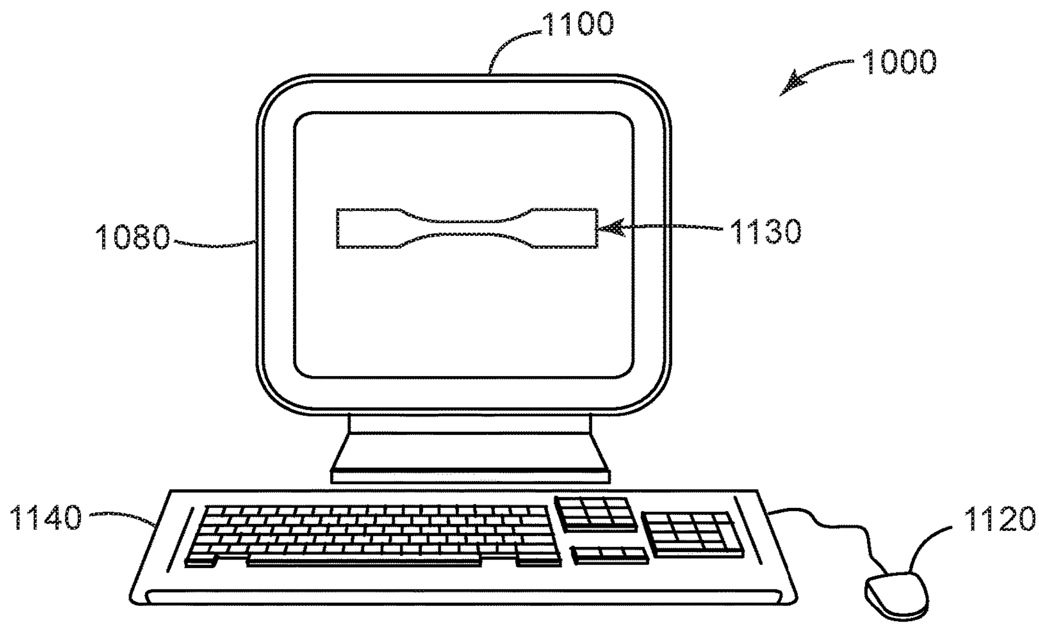
FIG. 10 is a schematic front view of an exemplary computing device 1000.
Figure 11:
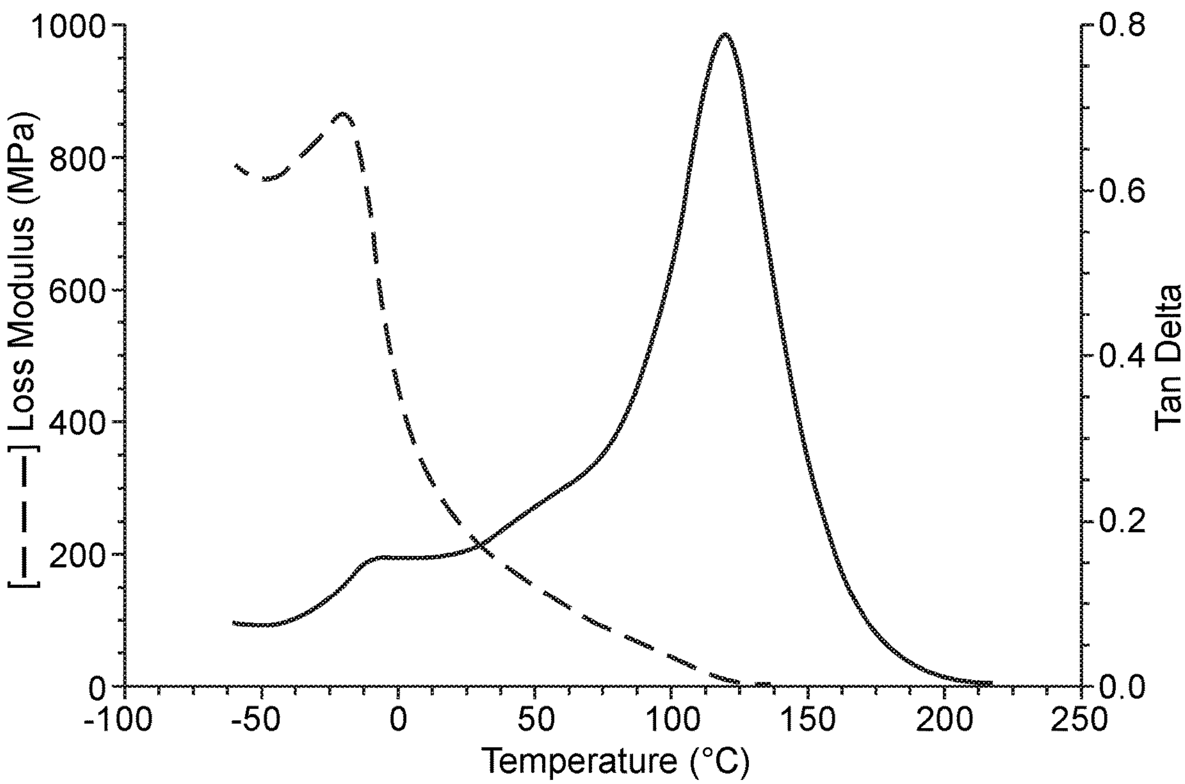
FIG. 11 is a dynamic mechanical analysis temperature sweep of the cured composition of Example 2.
Figure 12:
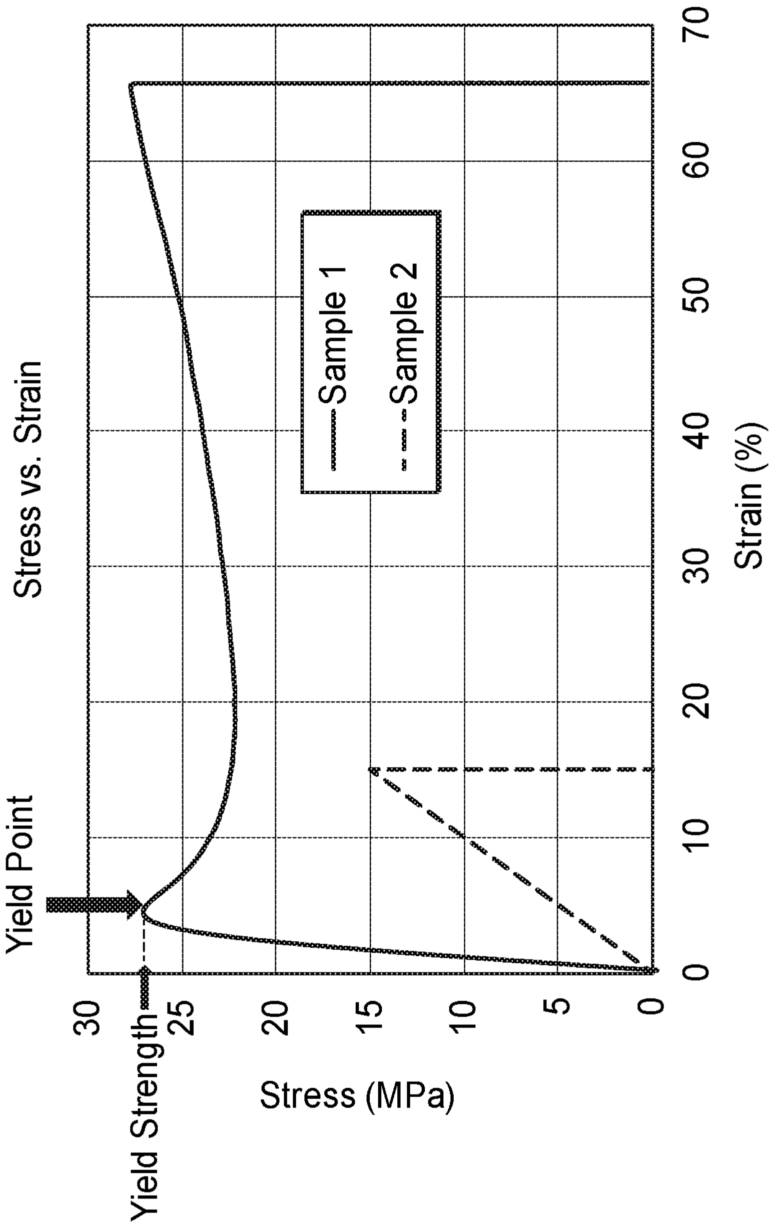
FIG. 12 is a stress-strain curve of a composition that exhibits a yield strength, a distinct peak prior to a plateau, in comparison to a composition that exhibits a maximum tensile strength in the absence of yielding.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, a tensile bar 1130 is shown on the display 1100.

Figure 6:
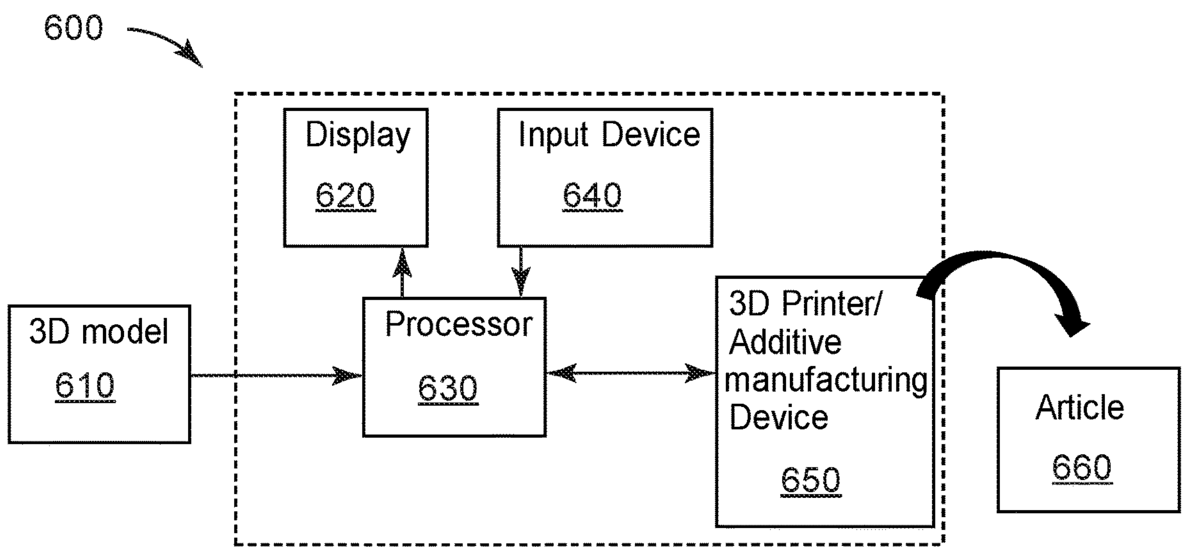
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., a tensile bar 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition as described herein.

Figure 7:
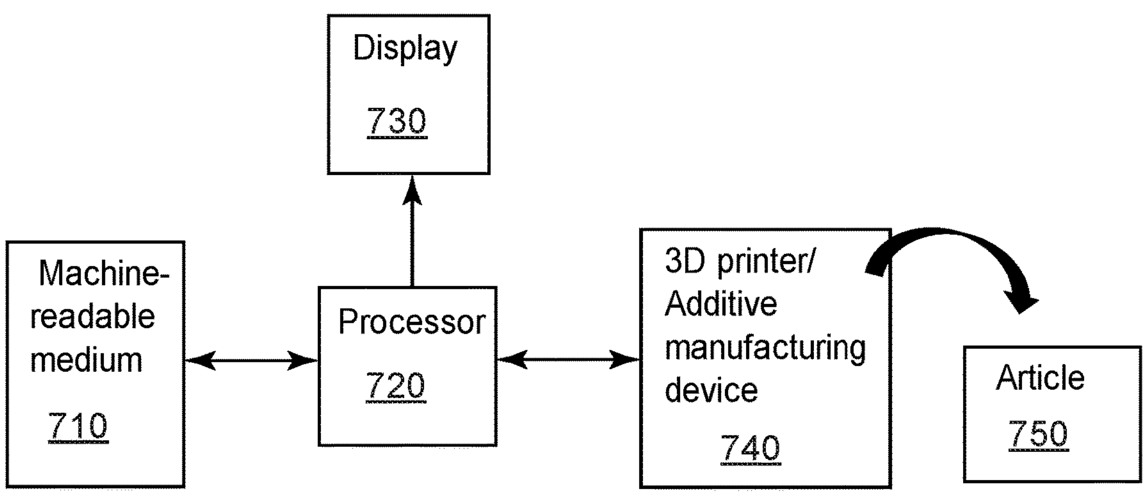
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., a tensile bar 1130 as shown on the display 1100 of FIG. 10) from the machine-readable medium 710.

Figure 8:
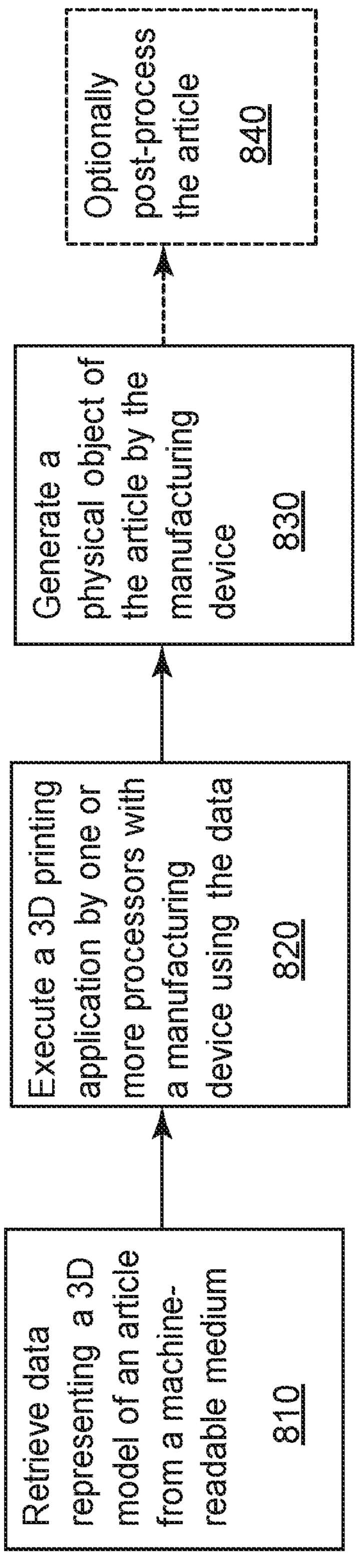
FIG. 8 is a high-level flow chart of an exemplary article manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition as described herein. One or more various optional post-processing steps 840 may be undertaken. Typically, remaining unpolymerized photopolymerizable component may be cured. In certain embodiments, the article comprises an orthodontic article.

Figure 9:
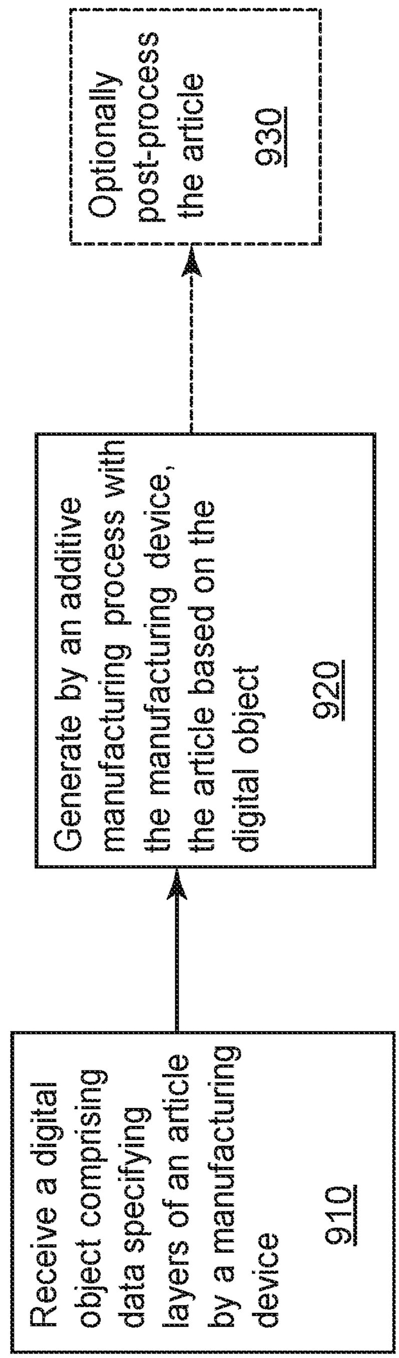
FIG. 9 is a high-level flow chart of an exemplary article additive manufacturing process.

Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930.

As used herein, "aliphatic group" means a saturated or unsaturated linear, branched, or cyclic hydrocarbon group. This term is used to encompass alkyl, alkenyl, and alkynyl groups, for example. The term "aliphatic/cycloaliphatic" means a compound or polymer that contains both an aliphatic group and a cycloaliphatic group.

As used herein, "alkyl" means a linear or branched, cyclic or acyclic, saturated monovalent hydrocarbon having from one to thirty-two carbon atoms, e.g., methyl, ethyl, 1-propyl, 2-propyl, pentyl, and the like.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, "aralkylene" refers to a divalent group that is an alkylene group substituted with an aryl group or an alkylene group attached to an arylene group. The term "alkarylene" refers to a divalent group that is an arylene group substituted with an alkyl group or an arylene group attached to an alkylene group. Unless otherwise indicated, for both groups, the alkyl or alkylene portion typically has from 1 to 20 carbon atoms, 1 to 10 carbon atoms, 1 to 6 carbon atoms, or 1 to 4 carbon atoms. Unless otherwise indicated, for both groups, the aryl or arylene portion typically has from 6 to 20 carbon atoms, 6 to 18 carbon atoms, 6 to 16 carbon atoms, 6 to 12 carbon atoms, or 6 to 10 carbon atoms.

As used herein, the term "glass transition temperature" ($T_g$), of a polymer refers to the transition of a polymer from a glassy state to a rubbery state and can be measured using Differential Scanning calorimetry (DSC), such as at a heating rate of 10° C. per minute in a nitrogen stream. When the $T_g$ of a monomer is mentioned, it is the $T_g$ of a homopolymer of that monomer. The homopolymer must be sufficiently high molecular weight such that the $T_g$ reaches a limiting value, as it is generally appreciated that a $T_g$ of a homopolymer will increase with increasing molecular weight to a limiting value. The homopolymer is also understood to be substantially free of moisture, residual monomer, solvents, and other contaminants that may affect the $T_g$. A suitable DSC method and mode of analysis is as described in Matsumoto, A. et. al., J. Polym. Sci. A., Polym. Chem. 1993, 31, 2531-2539.

As used herein, the term "hardenable" refers to a material that can be cured or solidified, e.g., by heating to remove solvent, heating to cause polymerization, chemical crosslinking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, "(meth)acrylic" is a shorthand reference to acrylic, methacrylic, or combinations thereof, and "(meth)acryl" is a shorthand reference to acryl and methacryl groups. "Acryl" refers to derivatives of acrylic acid, such as acrylates and methacrylates. By "(meth)acryl" is meant a monomer or polymer having at least one acryl or methacryl groups, and linked by an aliphatic segment if containing two or more groups. As used herein, "(meth)acrylate-functional compounds" are compounds that include, among other things, a (meth)acrylate moiety.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used. When actinic radiation can be used, the polymerizable composition is referred to as a "photopolymerizable composition".

As used herein, a "resin" contains all polymerizable components (monomers, oligomers and/or polymers) being present in a hardenable composition. The resin may contain only one polymerizable component compound or a mixture of different polymerizable compounds.

As used herein, the "residue of a diisocyanate", is the structure of the diisocyanate after the —NCO groups are removed. For example, 1,6-hexamethylene diisocyanate has the structure $OCN—(CH_2)_6—NCO$, and its residue, $R_{di}$, after removal of the isocyanate groups is $—(CH_2)_6—$.

TABLE 1

Materials

| Material designation | Description |
|---|---|
| 1-Adamantanol | Obtained from TCI America, Portland, OR. |
| 4-hydroxy-TEMPO | 4-hydroxy-2,2,6,6-tetramethylpiperidine 1-oxyl, obtained from Sigma Aldrich, St. Louis, MO. |
| Acetonitrile | Omnisolv HPLC grade obtained from EMD Millipore, a part of Merck KGaA, Darmstadt, Germany. |
| Ammonium formate | Obtained as a 5 M aqueous solution from Agilent Technologies, Waldbronn, Germany. |
| Anhydrous magnesium sulfate | Obtained from EMD Millipore, a part of Merck KGaA. |
| BHT | 2,6-di-t-butyl-4-methylphenol obtained from Alfa Aesar, Haverhill, MA. |
| CP 2201A | Caprolactone diol of about 2000 MW obtained from Perstorp, Warrington, UK. |
| CEA | 2-Carboxyethyl acrylate, obtained from Sigma-Aldrich, St. Louis, MO. |
| CHMA | Cyclohexyl methacrylate, from Alfa Aesar, Haverhill, MA. |
| CN991 | Aliphatic polyester urethane diacrylate oligomer, obtained from Sartomer. |
| DBTDL | Dibutyltin dilaurate, obtained from Sigma-Aldrich, St. Louis, MO. |
| DDDMA | 1,12-dodecanediol dimethacrylate obtained as "SR262" from Sartomer, Exton, PA. |
| Desmodur I (IPDI) | Isophorone diisocyanate, under trade designation "DESMODUR I" equivalent weight 111.11, molecular weight 222.22 g/mole, from Covestro LLC. |

TABLE 1-continued

| Material designation | Description |
|---|---|
| Materials | |
| Desmodur W (H12MDI) | Hydrogenated methylene diisocyanate, under trade designation "DESMODUR W", equivalent weight 131.25, molecular weight 262.5 g/mole, from Covestro LLC. |
| DiCPMA | Dicyclopentanyl methacrylate Obtained from TCI America, Portland, OR. |
| EHMA | 2-Ethyl hexyl methacrylate, obtained from Alfa Aesar. |
| Ethanol | Obtained from Spectrum Chemicals, New Brunswick, NJ. |
| Ethyl acetate | Obtained from EMD Millipore, a part of Merck KGaA. |
| Exothane-10 | A urethane (meth)acrylate polymer comprising a polyethylene oxide diol of about 400 MW, obtained as "EXOTHANE-10" from Esstech Inc., Essington, PA. |
| Exothane-108 | A urethane (meth)acrylate polymer comprising a polytetramethylene oxide diol of about 650 MW, obtained as "EXOTHANE-108" from Esstech Inc. |
| FR 44-56 | A butane diol adipate polyester diol of about 2000MW obtained as "FOMREZ 44-56" from Chemtura. |
| FR 55-56 | A neopentyl glycol adipate polyester diol of about 2000MW obtained as "FOMREZ 55-56" from Chemtura. |
| GAM | Glycerol acrylate methacrylate, CAS 1709-71-3, obtained from TCI America , Portland, OR |
| HEA | Hydroxyethyl acrylate, obtained from Alfa Aesar. |
| HEMA | Hydroxyethyl methacrylate, obtained from TCI America. |
| Hexanes | obtained from EMD Millipore, a part of Merck KGaA. |
| Hydroquinone | Obtained from Alfa Aesar. |
| IBOA | Isobornyl acrylate, obtained from Alfa Aesar. |
| IBOMA | Isobornyl methacrylate obtained as from San Esters/Kowa |
| SR833 S | Tricyclodecane dimethanol diacrylate obtained under the trade designation SR833S, from Sartomer, Exton PA |
| IEA | Isocyanatoethyl acrylate, MW 141.12, available under the trade designation "KARENZ AOI," from Showa Denko, Tokyo, Japan. |
| IEM | Isocyanatoethyl methacrylate, MW 155.15, available under the trade designation "KARENZ MOI," from Showa Denko. |
| IEM-EO | Isocyanatoethoxyethyl methacrylate, MW 199.2, available under the trade designation "KARENZ MOI-EG," from Showa Denko. |
| iPrOH | Isopropyl alcohol, obtained from EMD Millipore, a part of Merck KGaA. |
| KOH | Potassium hydroxide, obtained from Sigma Aldrich. |
| MDI | Product trade designation "MONDUR MLQ," an approximate 80:20 mixture of 4,4' and 2,4' diphenylmethane diisocyanate, equivalent weight 125.125, molecular weight 250.25, from Covestro LLC. |
| Methacrylic acid | Obtained from Sigma Aldrich. |
| Methylcyclohexane | Obtained from Sigma Aldrich. |
| NVP | 1-vinyl-2-pyrolidone, obtained from TCI Chemicals, Portland, OR. |
| P-510 | A 3-methyl-1,5-pentanediol (MPD) adipate polyester diol of about 500 MW obtained as "KURARAY POLYOL P-510" from Kuraray Co. Ltd., Tokyo, Japan. |
| P-1010 | A 3-methyl-1,5-pentanediol (MPD) adipate polyester diol of about 1000 MW obtained as "KURARAY POLYOL P-1010" from Kuraray Co. Ltd. |
| P-1020 | A 3-methyl-1,5-pentanediol (MPD) terephthalate polyester diol of about 1000 MW obtained as "KURARAY POLYOL P-1020" from Kuraray Co. Ltd |
| P-2010 | A 3-methyl-1,5-pentanediol (MPD) adipate polyester diol of about 2000 MW obtained as "KURARAY POLYOL P-2010" from Kuraray Co. Ltd. |
| P-2020 | A 3-methyl-1,5-pentane diol terephthalate diol of about 2000 MW obtained as "KURARAY POLYOL P-2020" from Kuraray. |
| P-2030 | A 3-methyl-1,5-pentane diol isophthalate diol of about 2000 MW obtained as "KURARAY POLYOL P-2030" from Kuraray. |
| P-2050 | A 3-methyl-1,5-pentanediol (MPD) sebecate (C10 diacid) polyester diol of about 2000 MW obtained as "KURARAY POLYOL P-2050" from Kuraray Co. Ltd. |
| P-3010 | A 3-methyl-1,5-pentanediol (MPD) adipate polyester diol of about 3000 MW obtained as "KURARAY POLYOL P-3010" from Kuraray Co. Ltd. |
| P-4010 | A 3-methyl-1,5-pentanediol (MPD) adipate polyester diol of about 4000 MW obtained as "KURARAY POLYOL P-4010" from Kuraray Co. Ltd. |
| P-5010 | A 3-methyl-1,5-pentanediol (MPD) adipate polyester diol of about 5000 MW obtained as "KURARAY POLYOL P-5010" from Kuraray Co. Ltd. |
| P-6010 | A 3-methyl-1,5-pentanediol (MPD) adipate polyester diol of about 6000 MW obtained as "KURARAY POLYOL P-6010" from Kuraray Co. Ltd. |
| C-2050 | A polycarbonate diol of about 1000 MW made with about a 9:1 mole ratio of 3-methyl-1,5-pentanediol (MPD): hexane diol (HD), (i.e., 90% MPD) obtained under the trade designation KURARAY POLYOL C-1090 |
| PBS | Phosphate buffered saline (PBS, 10X), pH = 7.4, obtained from Alfa Aesar. |
| Phenothiazine | Obtained from TCI America. |
| Priplast 1838 | A dimer acid based polyester diol of about 2000MW obtained as "PRIPLAST 1838" from Croda, Edison, NJ. |

TABLE 1-continued

| Materials | |
|---|---|
| Material designation | Description |
| Priplast 1900 | An ethylene glycol- hexane diol/adipate-azelate (C9 diacid) copolyester diol obtained as "PRIPLAST 1900" from Croda. |
| Propylene Carbonate | Obtained from Alfa Aesar. |
| Sodium bicarbonate | Obtained from EMD Millipore, a part of Merck KGaA. |
| SPP PC-205P-56 | A hexane diol-adipate diol of about 2000MW obtained as "STEPANPOL PC-205P-56" from Stepan, Northfield, IL. |
| Sulfuric acid | Obtained from EMD Millipore, a part of Merck KGaA. |
| Tetrahydrofuran | Omnisolv HPLC grade from EMD Millipore, a part of Merck KGaA. |
| Tinuvin 326 | Phenol, 2-(5-chloro-2H-benzotriazol-2-y1)-6-(1,1-dimethylethyl)-4-methyl, UV-absorber, obtained from BASF |
| TPO | 2,4,6-trimethylbenzoyldiphenylphosphine oxide photoinitiator obtained as "IRGACURE TPO" from BASF. |
| XK-672 | Zn based catalyst obtained as "K-KAT XK-672" from King Industries, Norwalk, CT. |

Characterization by Nuclear Magnetic Resonance (NMR) Spectroscopy

An Ultrashield 500 Plus FT NMR instrument from Bruker (Billerica, MA) was used to acquire $^1$H NMR (500 MHz) and $^{13}$C NMR (125 MHz) spectra. Chemical shifts (δ) are reported in ppm relative to $CDCl_3$. Abbreviations for splitting patterns are as follows; s (singlet); d (doublet); t (triplet); q (quartet); m (multiplet); br (broad); app (apparent) and combinations of these abbreviations.

Characterization by Gas Chromatography (GC)

Sample purity and product ratios were determined by gas chromatography (GC) and was performed using a Hewlett Packard (Palo Alto, CA) 6890 Series Plus gas chromatograph with a flame ionization detector and HP G1530A digital integrator. Sample injection was done with a 7683 series injector in conjunction with an injection volume of 2 microliters, injection port at a temperature of 250° C., and a split ratio of 20:1. A 30 m×0.53 mm×5 micrometer column obtained under the trade designation "RESTEX RTX-1" from Restek Corp. (Bellefonte, PA) was utilized with a flow rate of 12.4 mL/min He as the carrier gas with a temperature program of 50° C. to 230° C. at 15° C./min; 230° C. to 280° C. at 50° C./min; then hold at 280° C. for 2 min.

Preparation of Adamantyl-1-methacrylate (AdMA)

A 2 L, 3 neck round-bottom flask was fitted with a dean-stark trap with a condenser, magnetic stir bar, and a thermometer. 1-Adamantanol (252 g 1.650 mol), hydroquinone (0.3 g), methacrylic acid (455 g, 5.28 mmol), and methylcyclohexane (400 g) were added and the mixture was stirred. Sulfuric acid (10.5 g) was then added to the mixture, and then dry air was slowly bubbled into the mixture. The mixture was heated to reflux under constant bubbling of air for 26 hours, during which time the reaction product water was removed using the trap. The mixture was then cooled to room temperature, and slowly added to a mechanically stirred, ice-bath cooled mixture of 350 g KOH (6.2 mol) in 1000 g of deionized water and 500 g hexanes. After the addition was complete, the resulting mixture was separated using a separatory funnel, and extracted 1×500 mL hexanes. The combined organic extracts were washed with a saturated aqueous sodium bicarbonate solution, and then 20 mg of phenothiazine was added to the organic phase. This was then dried over anhydrous magnesium sulfate, filtered, and concentrated by rotary evaporation. The concentrate was then distilled under vacuum (BP=87-90° C., 0.3 torr), where the receiver flask contained 15 mg of 4-hydroxy-TEMPO, and 320 g of liquid was obtained. BHT (48 mg) was then added and dry air was bubbled into the clear product for 30 seconds before storage. $^1$H NMR: 5.99 (m, 1H), 5.45 (m, 1H), 2.14 (m, 9H), 1.87 (m, 3H), 1.64 (m, 6H). $^{13}$C NMR: 168.5, 138.1, 124.3, 80.4, 41.3, 36.3, 30.9, 18.4. $^1$H NMR was consistent with adamantyl-1-methacrylate. The purity was 98.4% according to gas chromatography.

Preparation of Polyester Diol Based Urethane (Meth) Acrylates

Urethane (Meth) acrylate Oligomers 1-23, 29-31, and 34-37 were prepared by reacting polyester diols with diisocyanates and end-capping with (meth)acrylate mono-ols. An illustrative reaction scheme is as follows:

4 IPDI/2 P-2010/2 HEMA (Polymer 11)

A 3 L three-necked round-bottom flask was charged with 1475.29 g heated polyester diol P-2010 (1.462 eq, 1009 hydroxyl equivalent weight (OH EW)), 324.91 g IPDI (2.9242 eq), 0.800 g BHT (400 ppm), and 0.500 XK-672 (250 ppm). The reaction of initial temperature 60° C., was heated under dry air to an internal setpoint of 100° C. (temperature reached at about 50 min). At 1 hour and 1 minutes, 199.80 g HEMA (1.5352 eq, 130.14 MW, a 5% stoichiometric excess) was added via an addition funnel at a steady rate over 30 minutes. At 6.5 hours into the reaction, an aliquot was checked by Fourier transform infrared spectroscopy (FTIR) and found to have no-NCO peak at 2265 $cm^{-1}$ and some of the product was poured out of the flask as a clear, viscous material, while the 1041.94 g that remained in the flask was diluted with 694.62 g IBOMA, to provide 1736.56 g of a 60:40 by weight mixture of Polymer 11:IBOMA.

This reaction scheme can also produce diisocyanate capped with (meth)acrylate mono-ols as a by-product.

Urethane (Meth) acrylate Oligomers 24-28 were prepared by reacting polyester diols with isocyanate-(meth)acrylates. An illustrative reaction scheme is as follows:

P-2010/IEM (Polymer 24)

A 500 mL three-necked round-bottom flask was charged with 260.02 g P-2010 (0.2577 eq, 1009 OH EW), 0.075 g BHT (400 ppm), and 0.075 g XK-672 (250 ppm) and heated to an internal temperature of about 60° C. under dry air. Then 39.98 g IEM (0.2577 eq, 155.15 MW) was added via an addition funnel over about 30 minutes. At 1 hour the reaction set point was raised to 80° C. and at 3 h into the reaction, an aliquot was checked by FTIR and found to have no-NCO peak at 2265 $cm^{-1}$ and the product was isolated as a clear, viscous material.

Polyurethane (meth)acrylates lacking polyester moieties (Monomers 32-33) were also be produced from diisocyanates capped with (meth)acrylate mono-ols. An illustrative synthesis is as follows:

IPDI/HEMA (Monomer 32)

A 5 L three-necked round-bottom flask was charged with 685.29 g IPDI (6.167 eq, 111.11 NCO EW), 0.613 g BHT, and 0.383 g XK-672 (250 ppm based on solids) at room temperature under dry air. Then without heating, all but 200 g of the 846.21 g (6.507 eq) HEMA was added over 2 hour and 52 minutes, with the internal temperature rising to a maximum of 86.5° C. At 2 hours and 57 minutes, the final 200 g of HEMA was added over about 30 min, at which time the internal was 67° C. The setpoint for the reaction was raised to 90° C., with this temperature being reached at 5*h* 33 minutes into the reaction. The reaction was run for an additional 9 h at 90° C., then allowed to cool to room temperature overnight. In the morning an aliquot was checked by FTIR and found to have a very small-NCO peak at 2265 $cm^{-1}$, and the reaction was packaged.

The aliphatic polyester diol based polyurethane acrylates and polyurethane acrylates lacking polyester moieties of Table 2 below were prepared by one of the methods as described above, using the amounts and types of materials indicated in the table.

Determination of HEMA-Diisocyanate-HEMA by-Product Concentration.

Determination of a concentration of HEMA-Diisocyanate-HEMA polymer was performed by liquid chromatography-mass spectrometry (LC/MS) on an Agilent 1260 Infinity Series liquid chromatography system (Agilent Technologies, Waldbronn, Germany) using an Agilent Poroshell 120 SB-C8 2.1 mm×50 mm 2.7 micrometer column eluted at 40° C. with a flow rate of 0.5 mL per minute. 2 microliter samples were injected and eluted with a linear gradient as described below. The water was Omnisolv HPLC grade from EMD Millipore, a part of Merck KGaA. The re-equilibration time between experiments was 5 minutes. Detection was with an Agilent 6130 Quadrupole LC/MS detector with electrospray ionization. Sample quantification was done by integration of the chromatographic peak detected at 500.3 m/z (M32, M-$NH_4^+$) or 540.3 m/z (M33, M-$NH_4^+$). Mass spectrometer parameters were in atmospheric pressure ionization-electrospray (API-ES) mode: capillary voltage 4 kV, nebulizer gas pressure 50 psig (345 kPa gauge), drying gas flow rate 10 liters per minute, drying gas temperature 300° C.

TABLE 2A

| Urethane (Meth) Acrylate Polymers & | | Isocyanate | | Diol | | | (meth)-acrylate mono-ol | |
|---|---|---|---|---|---|---|---|---|
| Monomers | Designation | Type | g | Type | g | OH EW | Type | g |
| 1 | 4 H12MDI/2 Priplast 1838/ /2HEMA | H12MDI | 18.81 | Priplast 1838 | 71.71 | 1000 | HEMA | 9.47 |
| 2 | 4 IPDI/2 P-1020/2 HEMA | IPDI | 39.02 | P-1020 | 87.79 | 500 | HEMA | 23.19 |
| 3 | 4 IPDI/2 P-2020/2 HEMA | IPDI | 81.39 | P-2020 | 370.23 | 1010.8 | HEMA | 48.38 |
| 4 | 4 IPDI/2 P-2030/2 HEMA | IPDI | 81.39 | P-2030 | 370.23 | 984.2 | HEMA | 48.38 |
| 5 | 4 IPDI/2.5 P-2020/1.5 HEMA | IPDI | 70.11 | P-2020 | 398.63 | 984.2 | HEMA | 31.26 |
| 6 | 4 IPDI/2 P-1010/2 HEMA | IPDI | 157.16 | P-1010 | 346.19 | 489.5 | HEMA | 96.64 |
| 7 | 4 IPDI/2 FR 55-56/2 HEMA | IPDI | 82.22 | FR 55-56 | 368.9 | 997 | HEMA | 48.88 |
| 8 | 4 IPDI/2 SPP PC-205P-56/2 HEMA | IPDI | 82.82 | SPP PC-205P-56 | 383.62 | 1029.36 | HEMA | 49.23 |
| 9 | 4 IPDI/2 FR 44-56/2 HEMA | IPDI | 98.47 | FR 44-56 | 441.55 | 996.45 | HEMA | 59.98 |
| 10 | 4 IPDI/3 Priplast 1900/1 HEMA | IPDI | 97.06 | Priplast 1900 | 324.10 | 494.71 | HEMA | 28.85 |
| 11 | 4 IPDI/2 P-2010/2 HEMA | IPDI | 324.91 | P-2010 | 1475.29 | 1009 | HEMA | 199.8 |
| 12 | 4 IPDI/1.5 P-2010/2.5 HEMA | IPDI | 115.96 | P-2010 | 394.9 | 1009 | HEMA | 89.13 |
| 13 | 4 IPDI/1.75 P-2010/2.25 HEMA | IPDI | 110.04 | P-2010 | 437.19 | 1009 | HEMA | 76.12 |
| 14 | 4 IPDI/2.5 P-2010/1.5 HEMA | IPDI | 84.07 | P-2010 | 477.16 | 1009 | HEMA | 38.77 |
| 15 | 4 IPDI/3 P-2010/1 HEMA | IPDI | 75.01 | P-2010 | 510.88 | 1009 | HEMA | 23.06 |
| 16 | 4 IPDI/2 P-2010/2 HEA | IPDI | 98.53 | P-2010 | 447.4 | 1009 | HEA | 54.06 |
| 17 | 4 H12MDI/2 P-2010/2 HEMA | H12MDI | 111.8 | P-2010 | 429.97 | 1009 | HEMA | 58.23 |
| 18 | 4 MDI/2 P-2010/2 HEMA | MDI | 107.57 | P-2010 | 433.7 | 1009 | HEMA | 58.74 |
| 19 | 4 IPDI/2 P-3010/2 HEMA | IPDI | 71.42 | P-3010 | 484.66 | 1508 | HEMA | 43.92 |
| 20 | 4 IPDI/1 P-3010/3 HEMA | IPDI | 56.42 | P-3010 | 191.52 | 1508 | HEMA | 52.06 |
| 21 | 4 IPDI/2 P-1010/2 HEMA | IPDI | 142.36 | P-1010 | 391.98 | 489.5 | HEMA | 65.65 |
| 22 | 4 IPDI/3 P-1010/1 HEMA | IPDI | 130.11 | P-1010 | 429.89 | 489.5 | HEMA | 40.00 |
| 23 | 4 IPDI/2 P-2050/2 HEMA | IPDI | 100.67 | P-2050 | 437.43 | 965.47 | HEMA | 61.9 |
| 24 | P-2010/IEM | IEM | 39.98 | P-2010 | 260.02 | 1009 | | |
| 25 | P-2010/IEM-EO | IEM-EO | 49.46 | P-2010 | 250.54 | 1009 | | |
| 26 | P-510/IEM | IEM | 115.42 | P-510 | 184.58 | 248.12 | | |
| 27 | P-1010/IEM | IEM | 72.2 | P-1010 | 227.8 | 489.5 | | |
| 28 | P-3010/IEM | IEM | 27.99 | P-3010 | 272.01 | 1508 | | |
| 29 | 4 IPDI/2 P-4010/2 HEMA | IPDI | 57.63 | P-4010 | 506.93 | 1954.7 | HEMA | 35.44 |
| 30 | 4 IPDI/2 P-5010/2 HEMA | IPDI | 46.93 | P-5010 | 524.21 | 2482.3 | HEMA | 28.86 |
| 31 | 4 IPDI/2 P-6010/2 HEMA | IPDI | 40.83 | P-6010 | 534.06 | 2906.74 | HEMA | 25.11 |
| M-32 | IPDI/HEMA | IPDI | 685.29 | — | — | — | HEMA | 846.81 |
| M-33 | H12MDI/HEMA | H12MDI | 310.25 | — | — | — | HEMA | 324.73 |
| 34 | 4 IPDI/2 P-4010/ 2 Glycerol Acrylate Methacrylate | IPDI | 55.51 | P-4010 | 488.3 | 1954.7 | GAM | 56.19 |
| 35 | 4 IPDI/2 P-3010/ 1 HEMA/ 1 Glycerol Acrylate Methacrylate | IPDI | 74.13 | P-3010 | 503.07 | 1508 | HEMA/GA M | 60.31 |
| 36 | P-2010/ IEA | IEA | 36.81 | P-2010 | 236.19 | 1009 | | |

TABLE 2A-continued

| Urethane (Meth) Acrylate Polymers & Monomers | Designation | Isocyanate Type | Isocyanate g | Diol Type | Diol g | Diol OH EW | (meth)-acrylate mono-ol Type | (meth)-acrylate mono-ol g |
|---|---|---|---|---|---|---|---|---|
| 37 | 4 IPDI/2 P-1010/2 HEA | IPDI | 93.09 | P-1010 | 205.60 | 490.81 | HEA | 51.32 |
| 38 | 4 IPDI/2 CP 2201A/2 HEMA | IPDI | 82.82 | CP 2201A | 367.95 | 987.32 | HEMA | 49.23 |
| 39 | 4IPDI/2P2010/ 2HEMA | IPDI | 1588.39 | C-2050 | 7034.88 | 984.2 | HEMA | 976.73 |

TABLE 2B

| Urethane (Meth) Acrylate Polymers & Monomers | Catalyst Type | Catalyst g | BHT g |
|---|---|---|---|
| 1 | DBTDL | 0.05 | 0 |
| 2 | DBTDL | 0.075 | 0 |
| 3 | DBTDL | 0.125 | 0 |
| 4 | DBTDL | 0.125 | 0.20 |
| 5 | DBTDL | 0.25 | 0.20 |
| 6 | XK-672 | 0.15 | 0.24 |
| 7 | DBTDL | 0.125 | 0.2 |
| 8 | DBTDL | 0.125 | 0.2 |
| 9 | XK-672 | 0.15 | 0.24 |
| 10 | XK-672 | 0.113 | 0.18 |
| 11 | XK-672 | 0.50 | 0.80 |
| 12 | XK-672 | 0.15 | 0.24 |
| 13 | XK-672 | 0.15 | 0.24 |
| 14 | XK-672 | 0.15 | 0.24 |
| 15 | XK-672 | 0.15 | 0.24 |
| 16 | XK-672 | 0.15 | 0.24 |
| 17 | XK-672 | 0.15 | 0.24 |
| 18 | XK-672 | 0.15 | 0.24 |
| 19 | XK-672 | 0.15 | 0.24 |
| 20 | XK-672 | 0.15 | 0.24 |
| 21 | XK-672 | 0.15 | 0.24 |
| 22 | XK-672 | 0.15 | 0.24 |
| 23 | XK-672 | 0.15 | 0.24 |
| 24 | XK-672 | 0.075 | 0.12 |
| 25 | XK-672 | 0.075 | 0.12 |
| 26 | XK-672 | 0.075 | 0.12 |
| 27 | XK-672 | 0.075 | 0.12 |
| 28 | XK-672 | 0.075 | 0.12 |
| 29 | XK-672 | 0.15 | 0.24 |
| 30 | XK-672 | 0.15 | 0.24 |
| 31 | XK-672 | 0.15 | 0.24 |
| M-32 | XK-672 | 0.383 | 0.613 |
| M-33 | XK-672 | 0.15 | 0.24 |
| 34 | XK-672 | 0.15 | 0.24 |
| 35 | XK-672 | 0.159 | 0.255 |
| 36 | XK-672 | 0.075 | 0.120 |
| 37 | XK-672 | 0.088 | 0.140 |
| 38 | DBTDL | 0.125 | 0.2 |

TABLE 3

| Solvent elution gradient | |
|---|---|
| Solvent | Time (min) |
| 6 mM ammonium formate in water | 0 |
| 6 mM ammonium formate in 98% acetonitrile/2% water | 3 |
| 6 mM ammonium formate in 98% acetonitrile/2% water | 5 |
| 89% acetonitrile 10% tetrahydrofuran 1% formic acid | 6 |

TABLE 3-continued

| Solvent elution gradient | |
|---|---|
| Solvent | Time (min) |
| 89% acetonitrile 10% tetrahydrofuran 1% formic acid | 8 |
| 6 mM ammonium formate in water | 9 |

Calibration samples were prepared by dissolution of 0.1000 g of polyurethane acrylate monomer M-32 and M-33 (described above) in a 100 mL volumetric flask using ethyl acetate. This solution was then diluted 1 mL into a 100 mL volumetric flask using acetonitrile to produce dilution 1. Dilution 1 was further diluted to ~2.00, 0.50, 0.10 and 0.012 ppm concentrations in acetonitrile and filtered through 0.22 micron PTFE syringe filters (Fisher Brand, Thermo Fisher Scientific, Hampton, NH). The calibration curve was linear from 2.0-0.012 ppm. Calibrations were performed directly preceding analytical samples.

Analytical samples were prepared by dissolution of 0.1-0.3 g of material in a 100 mL volumetric flask using ethyl acetate. This solution was then diluted 1 mL into a 100 mL volumetric flask using acetonitrile to produce dilution 1. Dilution 1 was filtered through 0.22 micron PTFE syringe filters (Fisher Brand) and analyzed as discussed above. In some cases, the polymer samples were diluted in (meth) acrylate monomer directly after synthesis and a pure sample of the polymer was not obtained. If this was the case, the concentration of HEMA/diisocyanate/HEMA in the original polymer was estimated by division of the found concentration of the HEMA/diisocyanate/HEMA in the sample by the concentration of polymer in the sample. The results for the amount of HEMA/diisocyanate/HEMA for each polymer are shown in Table 4 below.

TABLE 4

| Concentration of by-product | | | | |
|---|---|---|---|---|
| Urethane (Meth)acrylate Polymer | IPDI:Polyol: HEMA eq ratio | Polyol: HEMA eq ratio | IPDI: Polyol eq ratio | % HEMA-disocyanate-HEMA by-product |
| 9 | 4:2:2 | 1:1 | 2:1 | 5.7% |
| 10 | 4:2:2 | 1:1 | 2:1 | 5.6% |
| 11 | 4:2:2 | 1:1 | 2:1 | 5.4% |
| 12 | 4:1.5:2.5 | 1:1.7 | 2.7:1 | 12.5% |
| 13 | 4:1.75:2.25 | 1:1.3 | 2.3:1 | 8.6% |
| 14 | 4:2.5:1.5 | 1.7:1 | 1.6:1 | 1.4% |
| 15 | 4:3:1 | 3:1 | 1.3:1 | 0.2% |

TABLE 4-continued

| Concentration of by-product | | | | |
|---|---|---|---|---|
| Urethane (Meth)acrylate Polymer | IPDI:Polyol: HEMA eq ratio | Polyol: HEMA eq ratio | IPDI: Polyol eq ratio | % HEMA-disocyanate-HEMA by-product |
| 17 | 4*:2:2 *H12MDI | 1:1 | 2:1 | 8.2% HEMA-H12MDI-HEMA |
| 19 | 4:2:2 | 1:1 | 2:1 | 3.7% |
| 20 | 4:1:3 | 1:3 | 4:1 | 22.3% |
| 21 | 4:2.5:1.5 | 1.7:1 | 1.6:1 | 2.7% |
| 22 | 4:3:1 | 3:1 | 1.3:1 | 0.3% |
| 23 | 4:2:2 | 1:1 | 2:1 | 5.6% |
| 29 | 4:2:2 | 1:1 | 2:1 | 2.7% |
| 30 | 4:2:2 | 1:1 | 2:1 | 2.1% |
| 31 | 4:2:2 | 1:1 | 2:1 | 1.8% |

Polymer Molecular Weight Characterization Method:

The molecular weights of the polyester diol urethane (meth)acrylates were characterized using gel permeation chromatography (GPC). The GPC equipment consisted of an e2695 Separation Module and a 2414 dRI detector, both from Waters Corporation (Milford, MA). It was operated at a flow rate of 0.6 mL/min using tetrahydrofuran as the eluent. The GPC column was a HSPgel HR MB-M column also from Waters Corporation. The column compartment and differential refractive index detector were set to 35° C. The molecular weight standards were 10 EasiVial PMMA from Agilent Technologies (The $M_p$ values of the PMMA molecular weight standards used in the calibration curve ranged from 550 D to 1,568,000 g/mol.) The relative number average molecular weight (Mn) and weight average molecular weight (Mn) of selected oligomers/polymers, not including the (e.g. HEMA-diisocyanate-HEMA) by-product, are tabulated below in Table 5, in kiloDaltons (kD):

TABLE 5

| Molecular Weight | | | |
|---|---|---|---|
| Urethane (Meth)acrylate Polymer | Mn (kD) | Mw (kD) | Polydispersity |
| 9 | 8.7 | 13.2 | 1.5 |
| 10 | 9.2 | 14.4 | 1.6 |
| 11 | 8.2 | 12.5 | 1.5 |
| 12 | 7.3 | 10.6 | 1.4 |
| 13 | 7.8 | 11.6 | 1.5 |
| 14 | 10.1 | 16.3 | 1.6 |
| 15 | 14.4 | 24.6 | 1.7 |
| 16 | 8.2 | 12.7 | 1.5 |
| 17 | 10.5 | 16.0 | 1.5 |
| 18 | 9.6 | 14.9 | 1.6 |
| 19 | 11.3 | 17.8 | 1.6 |
| 20 | 9.1 | 13.2 | 1.4 |
| 21 | 6.0 | 9.3 | 1.5 |
| 22 | 8.6 | 14.6 | 1.7 |
| 23 | 8.4 | 12.7 | 1.5 |
| 24 | 4.0 | 7.8 | 1.9 |
| 25 | 4.2 | 7.9 | 1.9 |
| 26 | 1.1 | 2.0 | 1.8 |
| 27 | 1.9 | 3.9 | 2.0 |
| 28 | 5.5 | 11.1 | 2.0 |
| 29 | 13.1 | 21.1 | 1.6 |
| 30 | 15.6 | 25.7 | 1.6 |
| 31 | 18.2 | 30.1 | 1.7 |

General Procedure for Polymerizable Composition Preparation

The polymerizable compositions of Table 6 below were prepared by weighing the components in an amber jar, followed by rolling on a roller (having the trade designation "OLDE MIDWAY PRO18" and manufactured by Olde Midway) at 60° C. until mixed. Two parts by weight of TPO photoinitiator was added per 100 parts by weight of polymerizable resin to each of the compositions of Table 6.

General Procedure for Casting and Curing Polymerizable Composition

Each polymerizable composition of Table 6A and B below was poured into a silicone dogbone mold (Type V mold of 1 mm thickness, ASTM D638-14) for preparing tensile specimens, and a rectangular mold of dimensions (9.4 mm×25.4 mm×1 mm) for DMA 3-point bend test specimens. A 2 mil (0.05 mm) polyethylene terephthalate (PET) release liner (obtained under the trade designation "SCOTCHPAK" from 3M Company (St. Paul, MN)) was rolled on the filled mold, and the filled mold along with the liner was placed between two glass plates held by binder clips. The formulation was cured under a Asiga Pico Flash post-curing chamber (obtained from Asiga USA, Anaheim Hills, CA) for 30 minutes. The specimens were removed from the mold followed by additional light exposure for 30 minutes using the Asiga Pico Flash post-curing chamber. Specimens were then kept in an oven set at 100° C. for 30 minutes. The dogbone specimens were conditioned in phosphate-buffered saline (PBS, 1×, pH=7.4) for 24 hours at 37° C. The DMA 3-point bend test specimens were conditioned in de-ionized (DI) water for 48 hours at room temperature.

TABLE 6A

| Polymerizable Compositions | | | | | | |
|---|---|---|---|---|---|---|
| | Component 1 Urethane (meth)acrylate | % | Component 2 | % | Component 3 | % |
| Comp 1 (Exothane 10) | Exothane 10 | 30 | NVP | 20 | CEA | 50 |
| Comp 2 (CN991) | CN991 | 20 | NVP | 40 | CEA | 40 |
| Comp 3 (CN991) | CN991 | 30 | NVP | 60 | CN9782 | 10 |
| Control 4 (CN991) | CN991 | 50 | IBoMA | 50 | | |
| Comp 5 (Exothane 10) | Exothane 10 | 50 | IBoMA | 50 | | |
| Comp 6 (Exothane 8) | Exothane 108 | 50 | IBoMA | 50 | | |
| Control 7 (No Aliphatic Diol) | Polymer 2 | 50 | IBoMA | 50 | | |
| Control 8 (No Aliphatic Diol) | Polymer 3 | 50 | IBoMA | 50 | | |
| Control 9 (No Aliphatic Diol) | Polymer 4 | 50 | IBoMA | 50 | | |
| Control 10 (No Aliphatic Diol) | Polymer 5 | 50 | IBoMA | 50 | | |
| Control 11 (Low Tg Monomer) | Polymer 11 | 50 | EHMA | 50 | | |
| Ex. 1 | Polymer 36 | 50 | IBoMA | 50 | | |
| Ex. 2 | Polymer 7 | 50 | IBoMA | 50 | | |
| Ex. 3 | Polymer 8 | 50 | IBoMA | 50 | | |
| Ex. 4* | Polymer 9 | 50 | IBoMA | 50 | | |
| Ex. 5 | Polymer 1 | 50 | IBoMA | 50 | | |
| Ex. 6 | Polymer 10 | 50 | IBoMA | 50 | | |
| Ex. 7 | Polymer 11 | 50 | IBoMA | 50 | | |
| Ex. 8 | Polymer 12 | 50 | IBoMA | 50 | | |
| Ex. 9 | Polymer 13 | 50 | IBoMA | 50 | | |
| Ex. 10 | Polymer 14 | 50 | IBoMA | 50 | | |
| Ex. 11 | Polymer 15 | 50 | IBoMA | 50 | | |
| Ex. 12 | Polymer 16 | 50 | IBoMA | 50 | | |

TABLE 6A-continued

| Polymerizable Compositions | | | | | | |
|---|---|---|---|---|---|---|
| | Component 1 Urethane (meth)acrylate | % | Component 2 | % | Com-ponent 3 | % |
| Ex. 13 | Polymer 17 | 50 | IBoMA | 50 | | |
| Ex. 14 | Polymer 18 | 50 | IBoMA | 50 | | |
| Ex. 15 | Polymer 19 | 50 | IBoMA | 50 | | |
| Ex. 16 | Polymer 20 | 50 | IBoMA | 50 | | |
| Ex. 17 | Polymer 21 | 50 | IBoMA | 50 | | |
| Ex. 18 | Polymer 22 | 50 | IBoMA | 50 | | |
| Ex. 19 | Polymer 23 | 50 | IBoMA | 50 | | |
| Ex. 20 | Polymer 24 | 50 | IBoMA | 50 | | |
| Ex. 21 | Polymer 25 | 50 | IBoMA | 50 | | |
| Ex. 22 | Polymer 27 | 50 | IBoMA | 50 | | |
| Ex. 23 | Polymer 28 | 50 | IBoMA | 50 | | |
| Ex. 24 | Polymer 29 | 50 | IBoMA | 50 | | |
| Ex. 25 | Polymer 30 | 50 | IBoMA | 50 | | |
| Ex. 26 | Polymer 31 | 50 | IBoMA | 50 | | |
| Ex. 27 | Polymer 34 | 50 | IBoMA | 50 | | |
| Ex. 28 | Polymer 35 | 50 | IBoMA | 50 | | |
| Ex. 29 | Polymer 6 | 25 | Polymer 19 | 25 | IBoMA | 50 |
| Ex. 30 | Polymer 11 | 25 | Polymer 4 | 25 | IBoMA | 50 |
| Ex. 31 | Polymer 11 | 35 | Polymer 4 | 15 | IBoMA | 50 |
| Ex. 32 | Polymer 11 | 35 | Polymer 4 | 25 | IBoMA | 40 |
| Ex. 33 | Polymer 11 | 60 | IBoMA | 40 | | |
| Ex. 34 | Polymer 11 | 40 | IBoMA | 60 | | |
| Ex. 35 | Polymer 11 | 47.5 | M-32 | 5 | IBoMA | 47.5 |
| Ex. 36 | Polymer 15 | 47.5 | M-32 | 5 | IBoMA | 47.5 |
| Ex. 37 | Polymer 31 | 47.5 | M-32 | 5 | IBoMA | 47.5 |
| Ex. 38 | Polymer 11 | 45 | M-32 | 10 | IBoMA | 45 |
| Ex. 39 | Polymer 11 | 47.5 | M-33 | 5 | IBoMA | 47.5 |
| Ex. 40 | Polymer 11 | 45 | DDDMA | 10 | IBoMA | 45 |
| Ex. 41 | Polymer 11 | 45 | SR833 S | 10 | IBoMA | 45 |
| Ex. 42 | Polymer 11 | 50 | SR833 S | 2 | IBoMA | 48 |
| Ex. 43 | Polymer 11 | 50 | SR833 S | 5 | IBoMA | 45 |
| Ex. 44 | Polymer 11 | 40 | Polymer 24 | 10 | IBoMA | 50 |
| Ex. 45 | Polymer 11 | 40 | Polymer 26 | 10 | IBoMA | 50 |
| Ex. 46 | Polymer 11 | 40 | Polymer 27 | 10 | IBoMA | 50 |
| Ex. 47 | Polymer 15 | 40 | Polymer 26 | 10 | IBoMA | 50 |
| Ex. 48 | Polymer 11 | 50 | AdMA | 50 | | |
| Ex. 49 | Polymer 11 | 50 | DICPMA | 50 | | |
| Ex. 50 | Polymer 20 | 60 | IBoMA | 40 | | |
| Ex. 51 | Polymer 36 | 40 | IBoMA | 60 | | |
| Ex. 52 | Polymer 6 | 50 | CHMA | 50 | | |
| Ex. 53 | Polymer 6 | 70 | IBoMA | 30 | | |
| Ex. 54 | Polymer 37 | 40 | IBOA | 60 | | |
| Ex. 55 | Polymer 11 | 35 | Polymer 2 | 15 | IBoMA | 50 |
| Ex. 56 | Polymer 11 | 35 | Polymer 5 | 15 | IBoMA | 50 |

* Formulation phase separated.

TABLE 6B

| Blend of polyester urethane (meth)acrylate and polycarbonate urethane (meth)acrylate | | |
|---|---|---|
| Components | 57 | 58 |
| IBoMA | 50 | 50 |
| Polymer 39 | 16.25 | 15 |
| Polymer 21 | 26.25 | 26.25 |
| Monomer 32 | 7.5 | 10 |

General Procedure for Tensile Testing

PBS conditioned ASTM D638-14 type V dogbones were tested on an Instron 5944 (Instron, Norwood, MA) with a 500 N load cell. The test speed was 5 mm/minute, and the initial grip separation was 1 inch. The gage length was set to 1 inch (2.5 cm.) Five replicate samples for each formulation were tested, and the average value are reported. The tensile strength at yield was determined according to ASTM D638-14 (2014) and shown in Table 7 and 9 below. Elongation at break was determined from the crosshead movement of the grips.

General Procedure for the Determination of 3-Point Bend at 2% Strain Modulus Using Dynamic Mechanical Analysis Rectangular specimens, from a rectangular mold of dimensions (9.4 mm×25.4 mm×1 mm) as described above, were water conditioned by soaking in deionized water for 48 hours at a temperature of 22 to 25° C. and were tested in a TA instruments Q800 DMA equipped with a submersion 3-point bending clamp. The water conditioned rectangular specimens were placed in a water filled submersion fixture, and were equilibrated for 10 minutes at 37° C. A 2% strain was applied using a displacement rate of 8.5 mm/min, and then 3-point bend modulus was measured immediately using TA advantage software. This data is reported in Table 7 and 9.

TABLE 7

| Yield strength, elongation and flexure modulus of cast and cured compositions | | | |
|---|---|---|---|
| | Strength at Yield (MPa) | Elongation at Break (%) | 3-Point Bend Modulus (MPa) |
| Comp 1 (Exothane 10) | DNY | 32.0 | N.M |
| Comp 2 (CN991) | DNY | 25.5 | N.M |
| Comp 3 (CN991) | DNY | 1.3 | N.M |
| Control 4 (CN991) | 50.0 | 6.8 | 1384.0 |
| Comp 5 (Exothane 10) | DNY | 2.9 | 1662.0 |
| Comp 6 (Exothane 8) | 43.1 | 9.3 | 1027.0 |
| Control 7 (No Aliphatic Diol) | DNY | 2.8 | 2829.0 |
| Control 8 (No Aliphatic Diol) | DNY | 0.8 | N.M2 |
| Control 9 (No Aliphatic Diol) | DNY | 3.6 | 1420.0 |
| Control 10 (No Aliphatic Diol) | DNY | 1.4 | 1772.0 |
| Control 11 (Low Tg Monomer) | DNY | 71.6 | 52.3 |
| Ex. 1 | 19.7 | 100.9 | 573.6 |
| Ex. 2 | 25.0 | 50.6 | 681.4 |
| Ex. 3 | 19.8 | 82.2 | 634.4 |
| Ex. 4 | 21.3 | 66.6 | 727.2 |
| Ex. 5 | 26.1 | 39.7 | 608.9 |
| Ex. 6 | 24.6 | 69.0 | 705.7 |
| Ex. 7 | 22.5 | 118.6 | 629.4 |
| Ex. 8 | 30.4 | 56.5 | 929.2 |
| Ex. 9 | 25.4 | 69.3 | 792.1 |
| Ex. 10 | 15.9 | 185.3 | 368.4 |
| Ex. 11 | 13.7 | 230.1 | 461.4 |
| Ex. 12 | 16.8 | 85.5 | 468.8 |
| Ex. 13 | 20.5 | 41.6 | 689.9 |
| Ex. 14 | 20.1 | 76.0 | 643.8 |
| Ex. 15 | 16.0 | 125.6 | 502.6 |
| Ex. 16 | 32.6 | 18.4 | 1031.0 |
| Ex. 17 | 26.2 | 24.7 | 491.0 |
| Ex. 18 | 18.5 | 102.3 | 609.1 |
| Ex. 19 | 21.5 | 79.1 | 513.5 |
| Ex. 20 | 12.6 | 79.1 | 366.6 |
| Ex. 21 | 11.6 | 75.5 | 345.8 |
| Ex. 22 | 24.1 | 24.7 | 658.8 |
| Ex. 23 | 11.0 | 149.8 | 334.9 |
| Ex. 24 | 14.7 | 152.0 | 474.0 |
| Ex. 25 | 13.0 | 186.2 | 430.2 |
| Ex. 26 | 12.8 | 177.3 | 429.8 |
| Ex. 27 | 18.6 | 59.7 | 617.1 |
| Ex. 28 | 19.1 | 70.0 | 643.5 |
| Ex. 29 | 25.6 | 25.9 | 824.4 |
| Ex. 30 | 31.4 | 54.0 | 813.8 |
| Ex. 31 | 28.3 | 76.9 | 882.0 |
| Ex. 32 | 18.0 | 123.0 | 440.4 |
| Ex. 33 | 11.5 | 136.0 | 248.6 |
| Ex. 34 | 33.7 | 22.8 | 1148.0 |
| Ex. 35 | 25.9 | 35.9 | 821.8 |
| Ex. 36 | 17.0 | 91.7 | 566.1 |
| Ex. 37 | 15.5 | 115.4 | 511.0 |
| Ex. 38 | 30.3 | 20.5 | 777.6 |
| Ex. 39 | 25.3 | 48.5 | 679.4 |
| Ex. 40 | 23.4 | 32.9 | 777.2 |
| Ex. 41 | 26.7 | 35.2 | 842.3 |
| Ex. 42 | 21.9 | 68.4 | 708.2 |
| Ex. 43 | 21.7 | 64.5 | 657.1 |

TABLE 7-continued

| Yield strength, elongation and flexure modulus of cast and cured compositions | | | |
|---|---|---|---|
| | Strength at Yield (MPa) | Elongation at Break (%) | 3-Point Bend Modulus (MPa) |
| Ex. 44 | 16.4 | 64.5 | 511.6 |
| Ex. 45 | 26.1 | 43.6 | 571.9 |
| Ex. 46 | 21.2 | 56.2 | 586.5 |
| Ex. 47 | 18.2 | 69.7 | 563.9 |
| Ex. 48 | 20.4 | 85.1 | 552.8 |
| Ex. 49 | 12.8 | 116.8 | 188.5 |
| Ex. 50 | 25.6 | 37.9 | 753.9 |
| Ex. 51 | 19.8 | 53.7 | 561.9 |
| Ex. 52 | 24.8 | 50.7 | 452.5 |
| Ex. 53 | 16.8 | 54.4 | 335.1 |
| Ex. 54 | 21.2 | 75.2 | 407.0 |
| Ex. 55 | 32.3 | 40.6 | 916.9 |
| Ex. 56 | 29.3 | 31.1 | 931.9 |
| Ex. 57 | 36.6 | 29.6 | 1003.3 |
| Ex. 58 | 39.1 | 15.1 | 1165.0 |

N.M. Not measured
DNY: Did not yield.

Additive Manufacturing of Polymerizable Compositions

Unless otherwise noted, all 3D-printed examples were manufactured on an Asiga Max vat polymerization 3D printer with a LED light source of 385 nm available from Asiga USA, Anaheim Hills, CA.

Polymerizable compositions of Table 6 were utilized for 3D-printing with the exception that in addition to having two parts by weight of TPO photoinitiator added per 100 parts by weight of polymerizable resin, 0.025 parts by weight BHT and 0.25 parts by weight Tinuvin 326 was also added per 100 parts by weight of the polymerizable resin.

Tensile test bars of Type V according to ASTM D638-14 (2014) and DMA 3-point bend test specimens were manufactured on the 3D-printer. The resin bath of the printer was heated to 40° C. before photopolymerization to reduce the viscosity to be able to manufacture the tensile test bars. The following settings were used for the printing: slice thickness=50 μm; burn in layers=1; separation velocity=1.5 mm/s, separation distance=10 mm, approach velocity=1.5 mm/s. Table 8 describes the printer type, and the exposure time, burn-in time, and temperature used for printing the formulations. The printed parts were washed using propylene carbonate followed by isopropanol to remove unreacted resin. The printed part was then post-cured using Asiga Pico Flash post-curing chamber for 90 minutes on each side followed by heating in an oven at 100° C. for 30 minutes. The dogbone specimens were conditioned in phosphate-buffered saline (PBS, 1×, pH=7.4) for 24 hours at 37° C. The DMA 3-point bend test specimens were conditioned in DI water for 48 hours at room temperature.

TABLE 8

| Additive manufacturing conditions | | | |
|---|---|---|---|
| Polymerizable Composition of Table 6 | Exposure Time (sec) | Burn-in Time (sec) | Temperature (° C.) |
| Ex. 6 | 3.5 | 10 | 40 |
| Ex. 7 | 3.5 | 10 | 40 |
| Ex. 8 | 3 | 10 | 40 |
| Ex. 16 | 3 | 10 | 40 |
| Ex. 19 | 3 | 10 | 40 |

The printed samples were subjected to the same determination of flexure modulus using dynamic mechanical analysis, as previously described. The test results are as follows

TABLE 9

| Yield strength, elongation and flexure modulus of printed compositions | | | |
|---|---|---|---|
| Polymerizable Composition of Table 6 | Strength at Yield (MPa) | Elongation at Break (%) | 3-Point Bend Modulus (MPa) |
| Ex. 6 | 22.3 | 84.0 | 688.5 |
| Ex. 7 | 20.3 | 102.4 | 647.7 |
| Ex. 8 | 26.6 | 37.1 | 799.8 |
| Ex. 16 | 28.8 | 32.1 | 939.0 |
| Ex. 19 | 20.0 | 123.6 | 579.9 |

General Procedure for Determination of Loss Modulus and Tan Delta Using Dynamic Mechanical Analysis Dynamic mechanical analysis (DMA) was performed on rectangular cured samples (approximately 25.4 mm×9.4 mm×1 mm) using a TA Instruments model Q800 dynamic mechanical analyzer (TA Instruments (Newcastle, DE)) using a tension clamp in controlled strain mode, 0.2% strain, 0.02 N preload force, 125% force track, and 1 Hz. Temperature was swept at a rate of 2° C./min from −60° C. to 200° C. Samples were immersed in deionized water at 37° C. for 24 hours, at which time the samples were fully saturated with water prior to testing and tested immediately after removal from water. The peak loss modulus temperature and peak tan delta temperature were obtained from the temperature sweep data.

TABLE 10

| Physical Properties of Cured Compositions | | |
|---|---|---|
| Polymerizable Composition of Table 6 | Peak loss modulus (° C.) | Peak Tan delta (° C.) |
| Ex. 2 | −20 | 119 |
| Control 11 | −48 | 22 |
| Ex. 16 | >−50 | 130 |
| Ex. 48 | >−42 | 119 |

Additive Manufacturing of Aligner Articles from the Formulated Resin

Polymerizable composition 7 of Table 6 was photopolymerized on the Asiga Max printer with a LED light source of 385 nm. A stereolithography file format (STL file) of the aligner was loaded into the Asiga Composer software, and support structures were generated. The resin bath of the printer was heated to 40° C. before photopolymerization to reduce the viscosity to be able to manufacture the article. The following settings were used for the printing: slice thickness=50 μm; burn in layers=1; separation velocity=1.5 mm/min, burn-in exposure time=10 sec; exposure time=3 sec. The printed part was washed using propylene carbonate followed by isopropanol to remove unreacted resin. The printed specimen was then post-cured using an Asiga Pico Flash post-curing chamber for 90 minutes on each side. The photopolymerized aligners fit the models, showing precision of the additive manufacture part. The aligner had acceptable strength and flexibility.

What is claimed is:

1. An orthodontic article comprising the reaction product of a polymerizable composition, the polymerizable composition comprising:

a) at least 35 wt. % and no greater than 70 wt. % of one or more monofunctional (meth)acrylate monomers comprising a cyclic moiety, based on the total weight of organic components of the polymerizable composition, wherein at least one of the one or more monofunctional (meth)acrylate monomers is characterized by a homopolymer Tg of at least 60° C., and wherein the polymerizable composition comprises one or more monofunctional (meth)acrylate monomers having a log P value of less than 3 in a total amount of no greater than 10 wt. % of the total monofunctional (meth) acrylate monomers; and b) a urethane (meth)acrylate polymer comprising polymerized units of an aliphatic polyester diol, wherein the orthodontic article is an orthodontic alignment tray, wherein a total amount of monofunctional (meth)acrylate monomers is no greater than 70 wt. %, based on the total weight of organic components of the polymerizable composition, wherein the reaction product is characterized by a peak tan delta temperature of greater than 60° C., as determined according to dynamic mechanical analysis at a temperature sweep at a rate of 2° C./min from −60° C. to 200° C. after conditioning in deionized water at 37° C. for 24 hours, and wherein the Tg is measured by Differential Scanning calorimetry at a heating rate of 10° C. per minute.

2. The orthodontic article of claim 1 wherein the urethane (meth)acrylate polymer and the one or more monofunctional (meth)acrylate monomers are present at a weight ratio ranging from 2:1 to 1:2.

3. The orthodontic article of claim 1 wherein the one or more monofunctional (meth)acrylate monomers are further characterized by a log P value of greater than 1.

4. The orthodontic article of claim 1 wherein the one or more monofunctional (meth)acrylate monomers are present in an amount of at least 40 wt. % based on the total weight of the organic components of the polymerizable composition.

5. The orthodontic article of claim 1 wherein at least one of the one or more monofunctional (meth)acrylate monomers is characterized by a homopolymer Tg of at least 90° C.

6. The orthodontic article of claim 1 wherein the cyclic moiety is a cycloaliphatic group.

7. The orthodontic article of claim 1 wherein the urethane (meth)acrylate polymer comprises a reaction product of an aliphatic polyester diol, a diisocyanate, and a hydroxy functional methacrylate.

8. The orthodontic article of claim 1 wherein the urethane (meth)acrylate polymer comprises a reaction product of an aliphatic polyester diol and an isocyanate functional methacrylate.

9. The orthodontic article of claim 7 wherein the hydroxy functional (meth)acrylate is represented by formula HO-Q-$(A)_p$ wherein Q is a polyvalent organic linking group and A has the formula $—OC(=O)C(R_1)=CH_2$, wherein $R_1$ is H or alkyl of 1 to 4 carbon atoms, and p is at least 1 or 2.

10. The orthodontic article of claim 7 wherein the aliphatic polyester diol is represented by formula $$H[O—R_3—O—C(=O)—R_4—C(=O)]_m—O—R_3—OH,\ \text{or}$$

$$H[O—R_6—C(=O)]_n—O—R_5—O—(C(=O)]_n—R_6—O]_oH,$$

wherein $R_3$, $R_4$, $R_5$, and $R_6$ are independently aliphatic moieties comprising 2 to 40 carbon atoms, m ranges from 2 to 50, and n and o independently range from 4 to 25.

11. The orthodontic article of claim 1 wherein the urethane (meth)acrylate polymer is represented by formula $$(A)_p—Q—OC(O)NH—R_{di}—NH—C(O)—[O—R_{dOH}—OC(O)NH—R_{di}—NH—C(O)_r]—O—Q—(A)_p,\ \text{or}$$

$$(A)_p—Q—NHC(O)O—R_{dOH}—OC(O)NH—Q—(A)_p,$$

wherein: A is $-OC(=O)C(R_1)=CH_2$ wherein $R_1$ is H or alkyl of 1 to 4 carbon atoms, p is 1 or 2, Q is a polyvalent organic linking group, $R_{di}$ is a residue of a diisocyanate, $R_{dOH}$ is a residue of a polyester polyol, and r averages from 1 to 15.

12. The orthodontic article of claim 1 wherein the urethane (meth)acrylate polymer is an aliphatic urethane (meth) acrylate polymer or a urethane methacrylate polymer.

13. The orthodontic article of claim 1 wherein the urethane (meth)acrylate polymer has a weight average molecular weight (Mw) of 2,000 g/mol to 35,000 g/mol.

14. The orthodontic article of claim 1 wherein the polymerizable composition further comprises at least one second urethane (meth)acrylate polymer lacking aliphatic polyester moieties.

15. The orthodontic article of claim 14 wherein the second urethane (meth)acrylate is represented by formula $$(A)_p-Q-OC(=O)NH-R_{di}-NHC(=O)O-Q-(A)_p,$$

wherein: A is $-OC(=O)C(R_1)=CH_2$ wherein $R_1$ is H or alkyl of 1 to 4 carbon atoms, p is 1 or 2, Q is a polyvalent organic linking group, and $R_{di}$ is the residue of a diisocyanate.

16. The orthodontic article of claim 14 wherein the second urethane (meth)acrylate polymer is present at a weight ratio no greater than 25 wt. % relative to the weight of the urethane (meth)acrylate polymer.

17. The orthodontic article of claim 1 wherein the reaction product of the polymerizable composition is characterized by a peak loss modulus temperature of less than 0° C., as determined according to dynamic mechanical analysis after conditioning in deionized water at 37° C. for 24 hours.

18. The orthodontic article of claim 1 wherein the reaction product of the polymerizable composition is characterized by an elongation at break of 15% or greater and a tensile strength at yield of at least 10 MPa as determined according to ASTM D638-14 after conditioning in phosphate-buffered saline having a pH of 7.4, for 24 hours at a temperature of 37° C.

19. The orthodontic article of claim 1 wherein the reaction product of the polymerizable composition is characterized by a 3-point bend modulus of at least 100 MPa as determined according to dynamic mechanical analysis at 2% strain after conditioning in deionized water at 20-25° C. for 48 hours.

20. The orthodontic article of claim 1, wherein the polymerizable composition excludes ethylenically unsaturated components with acid functionality.

* * * * *